(12) United States Patent
Parenty et al.

(10) Patent No.: US 7,947,703 B2
(45) Date of Patent: May 24, 2011

(54) PHENANTHRIDINIUM DERIVATIVES AS DNA BINDING AGENTS

(75) Inventors: Alexis Parenty, Glasgow (GB); Leroy Cronin, Glasgow (GB); Robert Brown, Killearn (GB)

(73) Assignee: University Court of the University of Glasgow, Glasgow (GB)

( * ) Notice: Subject to any disclaimer, the term of this patent is extended or adjusted under 35 U.S.C. 154(b) by 1040 days.

(21) Appl. No.: 10/580,898

(22) PCT Filed: Nov. 26, 2004

(86) PCT No.: PCT/GB2004/005004
§ 371 (c)(1),
(2), (4) Date: Feb. 22, 2007

(87) PCT Pub. No.: WO2005/054241
PCT Pub. Date: Jun. 16, 2005

(65) Prior Publication Data
US 2007/0249652 A1   Oct. 25, 2007

(30) Foreign Application Priority Data
Nov. 26, 2003   (GB) .................................. 0327524.5

(51) Int. Cl.
*A61K 31/4745* (2006.01)
*C07D 471/06* (2006.01)
(52) U.S. Cl. ......................................... 514/285; 546/70
(58) Field of Classification Search .................. 514/285; 546/70
See application file for complete search history.

(56) References Cited

U.S. PATENT DOCUMENTS 5,401,847 A   3/1995 Glazer et al.
5,783,687 A   7/1998 Glazer et al.

FOREIGN PATENT DOCUMENTS

| EP | 1 223 226 A2 | 7/2002 |
|---|---|---|
| WO | WO 95/01341 | 1/1995 |
| WO | WO 96/03384 | 2/1996 |

OTHER PUBLICATIONS

CAPLUS Abstract Accession No. 1977:121139 & Comptes Rendus des Seances de l'Academie des Sciences, Serie D: Sciences Naturelles, 283(11): 1365-1367, "DNA intercalating drugs."
Yamazaki et al., Synthesis in the Diazasteroid Group VIIL Synthetic Studies of the 14,17-Diazasteroid System (1), J. Heterocyclic Chem., 16: 517 (1979).
Preston et al., "Further Investigations of Heterocyclic Alkylating Agents", J. Org. Chem., 28: 471-480 (1964).
Osbond et al., "Synthesis of Some Glyoxalino (1' : 2'-1 : 2)quinolines", J. Chem. Soc., 1853-1856 (1950).
Parenty et al., "General One-Pot, Three-Step Methodology Leading to an Extended Class of N-Heterocyclic Cations: . . . ", J. Org. Chem., 69: 5934-5946 (2004).
Lynch et al., "Synthesis, Biological Activity and Comparative Analysis of DNA Binding Affinities . . . ", Bioorganic & Medicinal Chemistry Letters, 11: 2643-2646 (2001).
Whittaker et al., "The interaction of DNA-targeted platinum phenanthridinium complexes with DNA", Nucleic Acids Research, 26(17): 3933-3939 (1998).
Koyama et al,, "Polycyclic N-Hetero Compounds. VI. Synthesis of 11,13,15-Triazasteroidal Compounds . . . ", Chem. Pharm. Bull., 23(9): 2015-2018 (1975).

*Primary Examiner* — Charanjit S Aulakh
(74) *Attorney, Agent, or Firm* — Patrick J. Hagan; Dann, Dorfman, Herrell and Skillman, P.C.

(57) ABSTRACT

Disclosed are new classes of phenanthridinium derivatives, most notably dihydro-imidazo-phenanthridinium (DIP) compounds. The compounds are prepared by the reaction of the middle b ring of a phenanthridinium core with primary amines to form the DIP compounds. This reaction can also be applied to other classes of starting compounds which comprise a 6-membered ring aromatic heterocycle having a ring nitrogen and at least one alpha hydrogen atom which can be reacted with a primary amine. Also disclosed is a method of using the DIP compounds for treatment of ovarian cancer.

25 Claims, 4 Drawing Sheets

PHENANTHRIDINIUM DERIVATIVES AS DNA BINDING AGENTS

FIELD OF THE INVENTION

The present invention relates to heterocyclic aromatic compounds, and more particularly to phenanthridinium derivatives such as dihydro-imidazo-phenanthridinium (DIP) compounds. The present invention further relates to methods of making these compounds and their uses, in particular as DNA binding agents and as pharmaceuticals.

BACKGROUND OF THE INVENTION

Heterocyclic rings are present as fundamental components in the skeletons of more than half of the biologically active compounds produced by nature. With this in mind, there have been great efforts to discover and optimise new reactions that will facilitate the construction of heterocycles, especially when the methodology leads to a new type of N-based heterocycle. A facile route to a new family of heterocycles opens the possibility of finding new types of biologically active units that can be used in the generation of libraries of compounds, or for use in the development of new methodologies to be applied in organic synthesis.

Yamazaki et al (J. Heterocyclic Chem., 16: 517-525, 1979) discloses the synthesis of Dihydro-Benzo[f]Imidazo[1,2-a]quinoline in three steps with an overall yield of 40%. The compounds produced also have the disadvantage that they are not functionalised.

Koyama et al (Chem. Pharm. Bull., 23(9):2015-2018, 1975) discloses the synthesis of dihydro-imidazo-benzo [h]quinazolinium in three steps with one example of substitution at one position on the molecule.

Preston et al (J. Med. Chem., 471-480, 1964) discloses the synthesis of dihydro-imidazo-quinolinium in three steps at very low yield (10%).

Osbond (J. Chem. Soc., 1853-1856, 1950) also discloses the synthesis of dihydro-imidazo-quinolinium in four steps.

U.S. Pat. Nos. 5,401,847 and 5,783,687 (Glazer et al) relate to fluorescent compounds that are not based on substituted phenanthridinium derivatives but which have the property of binding DNA.

EP 1 223 226 A (Tosho Corporation) discloses a family of molecules in which a phenanthridinium compound is linked to two further heterocyclic ring systems, see Formula 1. The phenanthridinium portion of the compound consists of a three ring heterocycle with a phenyl group in the alpha position relative to the heterocyclic nitrogen.

WO 95/01341 (Abbott Laboratories) discloses phenanthridinium compounds that consist of three ring heterocycle with a phenyl group in the alpha position relative to the heterocyclic nitrogen and which have two amine substituents on the first and third rings. These compounds are disclosed as DNA intercalators.

Chemical abstract numbers 1977:121139 (Roques et al, 1976) relates to a phenanthridinium compounds which is a three ring heterocycle with a phenyl group in the alpha position relative to the heterocyclic nitrogen.

SUMMARY OF THE INVENTION

Broadly, the present invention concerns new classes of heterocyclic aromatic cationic compounds, and in particular new classes of phenanthridinium derivatives, most notably dihydro-imidazo-phenanthridinium (DIP) compounds. These findings are based on the reaction of the middle b ring of a phenanthridinium core with primary amines to form DIP compounds (Formula A) or secondary amines to form 2-aminoalkyl phenanthridinium derivatives (Formula B). These reactions can also be applied to other classes of starting compounds which comprise a 6-membered ring aromatic heterocycle having a ring nitrogen and at least one alpha hydrogen atom which can be reacted with a primary or secondary amine.

Moreover, analogous reactions can be carried to produce dihydro-thiazoles, e.g. by reaction with a sulphate such as sodium sulphate $Na_2S$, and to produce dihydro-oxazoles, e.g. by reaction with a hydroxide such as KOH.

Typically, the chemistry disclosed herein has the advantage that is amenable to scaling up to large scale production as it does not involve any particularly hazardous reaction procedures. Further, the one pot reactions disclosed herein are usually carried out at room temperature and usually take less than 12 hours, with the result that the energetic cost of the industrialization process may be quite low.

In general, N-based heteroaromatic cations are highly interesting compounds due to their reactivity and biological properties. For instance, molecules containing a phenanthridinium core are one important subset of heteroaromatic cations with applications as drugs (topoisomerase inhibitors and DNA targeting agents), dyes and probes due to their high affinity for DNA. Moreover, a simple purification method (i.e. filtration of the reaction medium and wash) may make them very good candidates for combinatorial chemistry. Finally, because of the highly effective hydride transfer of the intermediaries in forming the phenanthridinium derivatives, there may be applications in non-enzymatic redox transformation, e.g. the reduction of ketones, sulfonatates, arenediazoniums and aldehydes.

A first class of compounds represented herein by Formula A are based on the ring extension of the heteroaromatic middle b ring of the phenanthridinium core, typically forming a new 5-8 membered ring, and more preferably a five or six membered ring. The new ring may comprise a dihydro-imidazolium, a dihydro-thiazolium, a dihydro-oxazolium moiety or a tetrahydro-pyrimidinium moiety, depending on whether the reaction is carried out with a primary amines or a sulphate or hydroxide compound to introduce a nitrogen, a sulphur or an oxygen heteroatom respectively. A second class of compounds represented by Formula B are based on the reaction of the heteroaromatic middle b ring of the phenanthridinium core with secondary amines, followed by an intramolecular rearrangement process.

In other aspects, the present invention provides methods for synthesising the compounds of the invention. The inventors have also elucidated the mechanisms of these reactions which are unprecedented. The mechanisms provide a basis for extending the specific reaction described herein to the synthesis of other types of heterocyclic aromatic cationic compounds.

Accordingly, in a first aspect, the present invention provides a compound represented by Formula A:

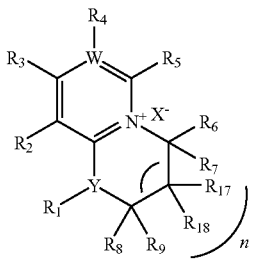

wherein:
n=0, 1, 2 or 3 such that:
when n=0, the substituents $R_{17}$ and $R_{18}$ and the carbon atom to which they are bonded are not present; and
when n is 1, 2 or 3, the substituents $R_{17}$ and $R_{18}$ present on the respective carbon atom(s) may be the same or different and are independently selected from hydrogen or a substituent as define herein;
W is C or N, such that when W is N, $R_4$ is a lone pair of electrons;
Y is selected from N, O or S, such that:
when Y is C or S, $R_1$ is a lone pair of electrons; and
when Y is N, $R_1$ is selected from:
hydrogen,
$C_{1-7}$alkyl, optionally substituted with one or more substituents as defined herein, e.g. a group which is a substituted or unsubstituted $C_{1-7}$alkyl, $C_{1-7}$haloalkyl, $C_{1-7}$hydroxyalkyl, $C_{1-7}$carboxyalkyl, $C_{1-7}$aminoalkyl group,
$C_{1-7}$cycloalkyl, optionally substituted with one or more substituents as defined herein,
$C_{1-7}$cycloalkyl-$C_{1-7}$alkyl, optionally substituted with one or more substituents as defined herein,
$C_{5-20}$aryl, optionally substituted with one or more substituents as defined herein, e.g. $C_{5-20}$-carboaryl or $C_{5-20}$heteroaryl,
$C_{1-7}$alkyl-$C_{5-20}$aryl and $C_{5-20}$haloaryl, optionally substituted with one or more substituents as defined herein,
$C_{5-20}$aryl-$C_{1-7}$alkyl, optionally substituted with one or more substituents as defined herein,
$C_{3-20}$heterocyclyl, optionally substituted with one or more substituents as defined herein,
or a linking group to form a multimeric compound in which a plurality of compounds represented by Formula A and/or Formula B are covalently bonded together, e.g. via their respective $R_1$ substituents (Formula A) or via their $R_6$ or $R_7$ substituents (Formula B) or via a spacer group;
independently $R_2$ and $R_3$ and/or $R_4$ and $R_5$ together can form an aromatic carbon or heterocyclic ring structure, optionally substituted with one or more aromatic substituents as defined herein, or $R_2$, $R_3$, $R_4$ and $R_5$ are independently selected from an aromatic substituent as defined herein;
$R_6$ and $R_7$ are independently selected from hydrogen or independently or together can be a substituent as defined herein;
$R_8$ and $R_9$ are independently selected from hydrogen or independently or together can be a substituent as defined herein;
wherein when $R_{17}$ and $R_{18}$ are present, they are independently selected from hydrogen or independently or together can be a substituent as defined herein; and
one of the substituents $R_6$ and $R_7$ which is present on the carbon atom at the alpha position to the aromatic ring can form a double bond with one of the substituents $R_8$ and $R_9$ or $R_{17}$ and $R_{18}$ which is present on the carbon atom at the beta position to the aromatic ring; and
$X^-$ is an anionic moiety, such as halogen (e.g. $Cl^-$, $Br^-$ or $I^-$), tosylate or mesylate.

In this aspect of the invention, preferred compounds represented by Formula A comprise a 5 or 6 membered ring extension, e.g. as produced when n=0 or 1 respectively. Alternatively or additionally, further preferred compounds are provided when W is a carbon atom.

Other preferred compounds of Formula A are provided when the Y substituent is N and/or n=0, so that the substituents $R_{17}$ and $R_{18}$ and the carbon atom to which they are bonded are not present and a 5-membered ring is formed.

In a further aspect, the present invention provides a compound represented by Formula Ai:

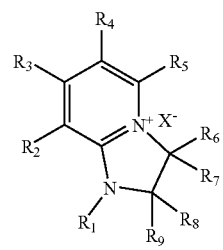

wherein:
$R_1$ is selected from:
hydrogen,
$C_{1-7}$alkyl optionally substituted with one or more substituents as defined herein, e.g. a group which is a substituted or unsubstituted $C_{1-7}$alkyl, $C_{1-7}$haloalkyl, $C_{1-7}$hydroxyalkyl, $C_{1-7}$carboxyalkyl, $C_{1-7}$aminoalkyl group, $C_{1-7}$cycloalkyl, optionally substituted with one or more substituents as defined herein,
$C_{1-7}$cycloalkyl-$C_{1-7}$alkyl, optionally substituted with one or more substituents as defined herein,
$C_{5-20}$aryl, optionally substituted with one or more substituents as defined herein, e.g. $C_{5-20}$carboaryl or $C_{5-20}$heteroaryl,
$C_{1-7}$alkyl-$C_{5-20}$aryl and $C_{5-20}$haloaryl, optionally substituted with one or more substituents as defined herein,
$C_{5-20}$aryl-$C_{1-7}$alkyl, optionally substituted with one or more substituents as defined herein,
$C_{3-20}$heterocyclyl, optionally substituted with one or more substituents as defined herein,
or a linking group to form a multimeric compound in which a plurality of compounds represented by Formula A and/or Formula B are covalently bonded together, e.g. via their respective $R_1$ substituents (Formula A) or via their $R_6$ or $R_7$ substituents (Formula B) or via a spacer group;
independently $R_2$ and $R_3$ and/or $R_4$ and $R_5$ together can form an aromatic carbon or heterocyclic ring structure, optionally substituted with one or more aromatic substituents as defined herein, or $R_2$, $R_3$, $R_4$ and $R_5$ are independently selected from an aromatic substituent as defined herein;
$R_6$ and $R_7$ are independently selected from hydrogen or independently or together can be a substituent as defined herein;
$R_8$ and $R_9$ are independently selected from hydrogen or independently or together can be substituent as defined herein;

wherein one of $R_6$ and $R_7$ and one of $R_8$ and $R_9$ can together form a double bond; and, $X^-$ is an anionic moiety, such as halogen (e.g. $Cl^-$, $Br^-$ or $I^-$), tosylate or mesylate.

In a further aspect, the present invention provides a compound represented by Formula Aii:

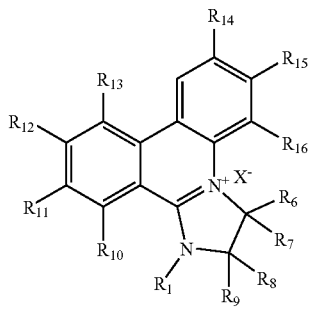

wherein:

$R_1$ is selected from:

hydrogen, $C_{1-7}$alkyl optionally substituted with one or more substituents as defined herein, e.g. a group which is a substituted or unsubstituted $C_{1-7}$alkyl, $C_{1-7}$haloalkyl, $C_{1-7}$hydroxyalkyl, $C_{1-7}$carboxyalkyl, $C_{1-7}$aminoalkyl group, $C_{1-7}$cycloalkyl, optionally substituted with one or more substituents as defined herein, $C_{1-7}$cycloalkyl-$C_{1-7}$alkyl, optionally substituted with one or more substituents as defined herein, $C_{5-20}$aryl, optionally substituted with one or more substituents as defined herein, e.g. $C_{5-20}$-carboaryl or $C_{5-20}$heteroaryl, $C_{1-7}$alkyl-$C_{5-20}$aryl and $C_{5-20}$haloaryl, optionally substituted with one or more substituents as defined herein, $C_{5-20}$aryl-$C_{1-7}$alkyl, optionally substituted with one or more substituents as defined herein, $C_{3-20}$heterocyclyl, optionally substituted with one or more substituents as defined herein, or a linking group to form a multimeric compound in which a plurality of compounds represented by Formula A and/or Formula B are covalently bonded together, e.g. via their respective $R_1$ substituents (Formula A) or via their $R_6$ or $R_7$ substituents (Formula B) or via a spacer group;

$R_6$ and $R_7$ are independently selected from hydrogen or independently or together can be a substituent as defined herein;

$R_8$ and $R_9$ are independently selected from hydrogen or, independently or together can be substituent as defined herein;

wherein one of $R_6$ and $R_7$ and one of $R_8$ and $R_9$ can together form a double bond; and $R_{10}$, $R_{11}$, $R_{12}$, $R_{13}$, $R_{14}$, $R_{15}$ and $R_{16}$ are independently selected from hydrogen or an aromatic substituent as defined herein; and $X^-$ is an anionic moiety, such as halogen (e.g. $Cl^-$, $Br^-$ or $I^-$), tosylate or mesylate.

In the present invention, preferred examples of linking groups are $C_{1-7}$alk-di-yl, piperazin-di-yl, (N,N-$C_{1-7}$ dialkylenen)$C_{1-7}$alkylene amine bonding to the $R_1$ group of a compound of Formula A or the $R_6$ and/or $R_7$ group of a compound of Formula B.

Examples of compounds represented by Formula A, Ai and Aii are set out below and include the following compounds:

1-(4-Methoxy-benzyl)-2,3-dihydro-1H-imidazo[1,2-f] phenanthridinium bromide;

1-(2-Hydroxy-ethyl)-2,3-dihydro-1H-imidazo[1,2-f] phenanthridin-4-ylium bromide;

2,3-Dihydro-1H-imidazo[1,2-f]phenanthridin-4-ylium bromide;

1-Isopropyl-2,3-dihydro-1H-imidazo[1,2-f]phenanthridin-4-ylium bromide;

1-Cyclopropyl-2,3-dihydro-1H-imidazo[1,2-f]phenanthridin-4-ylium bromide;

1-(4-Methoxy-phenyl)-2,3-dihydro-1H-imidazo[1,2-f] phenanthridin-4-ylium bromide;

1-Phenyl-2,3-dihydro-1H-imidazo[1,2-f]phenanthridin-4-ylium bromide; and 1-paramethoxyaniline-2,3-dihydro-1H-imidazo[1,2-f] phenanthridin-4-ylium bromide.

1-Methoxycarbonylmethyl-2,3-dihydro-1H-imidazo[1,2-f] phenanthridin-4-ylium bromide.

1-(1-Methoxycarbonyl-2-phenyl-ethyl)-2,3-dihydro-1H-imidazo[1,2-f]phenanthridin-4-ylium bromide.

1-Benzyl-2,3-dihydro-1H-imidazo[1,2-f]phenanthridin-4-ylium bromide.

1-(2-Mercapto-ethyl)-2,3-dihydro-1H-imidazo[1,2-f] phenanthridin-4-ylium bromide.

3-(4-Methoxy-benzyl)-2,3-dihydro-1H-imidazo[1,2-a] quinolin-10-ylium bromide.

1-(4-Methoxy-benzyl)-2,3-dihydro-1H-imidazo[2,1-a]isoquinolin-4-ylium bromide.

1-(4-Methoxy-benzyl)-2,3-dihydro-1H-imidazo[1,2-a]pyridin-4-ylium bromide.

1-Propyl-2,3-dihydro-1H-imidazo[1,2-f]phenanthridin-4-ylium bromide.

1-(2-Hydroxy-1-methyl-ethyl)-2,3-dihydro-1H-imidazo[1,2-f]phenanthridin-4-ylium bromide.

1-[1-(4-Methoxy-phenyl)-ethyl]-2,3-dihydro-1H-imidazo [1,2-f]phenanthridin-4-ylium bromide.

7-Bromo-1-(4-methoxy-benzyl)-2,3-dihydro-1H-imidazo[1,2-f]phenanthridin-4-ylium bromide.

1-(4-Ethyl-phenyl)-2,3-dihydro-1H-imidazo[1,2-f]phenanthridin-4-ylium bromide.

1-Hexyl-2,3-dihydro-1H-imidazo[1,2-f]phenanthridin-4-ylium bromide.

1-Dodecyl-2,3-dihydro-1H-imidazo[1,2-f]phenanthridin-4-ylium bromide.

1-Octadecyl-2,3-dihydro-1H-imidazo[1,2-f]phenanthridin-4-ylium bromide.

1-(3,3-Diphenyl-propyl)-2,3-dihydro-1H-imidazo[1,2-f] phenanthridin-4-ylium bromide.

1-(4-Methoxy-benzyl)-2,3-dihydro-1H-imidazo[1,2-c] quinazolin-4-ylium bromide.

In a further aspect, the present invention provides a compound represented by Formula B:

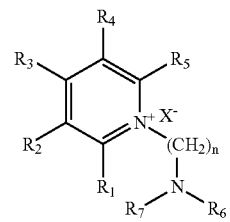

wherein:

n is 2 to 5, more preferably 2-3, and most preferably 2;

$R_1$ is hydrogen or an aromatic substituent as defined herein;

independently $R_2$ and $R_3$ and/or $R_4$ and $R_5$ together can form an aromatic carbon or heterocyclic ring structure, optionally substituted with one or more aromatic substituents as defined herein, or $R_2$, $R_3$, $R_4$ and $R_5$ are independently selected from an aromatic substituent as defined herein;

$R_6$ and $R_7$ are independently a substituent as defined herein or a linking group to form a multimeric compound in which a plurality of compounds represented by Formula A and/or Formula B are covalently bonded together, e.g. via their respective $R_1$ substituents (Formula A) or via their $R_6$ or $R_7$ substituents (Formula B) or via a spacer group;

$X^-$ is an anionic moiety, such as halogen (e.g. $Cl^-$, $Br^-$ or $I^-$), tosylate or mesylate.

Examples of compounds represented by Formula B are set out below and include:

5-(2-tert-butylamino-ethyl)-phenanthridinium bromide;

5-(2-Piperidin-1-yl-ethyl)-phenanthridinium bromide;

piperazine phenanthridinium derivatives;

hydroxylamine derivatives;

1,5,9-triaza-Cyclododecane.

In a further aspect, the present invention provides a compound represented by Formula Bi:

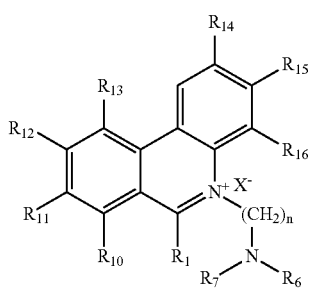

wherein:

n is 2 to 5, more preferably 2-3, and most preferably 2;

$R_1$ is hydrogen or an aromatic substituent;

$R_6$ and $R_7$ are independently hydrogen, a substituent as defined herein or a linking group to form a multimeric compound in which a plurality of compounds represented by Formula A and/or Formula B are covalently bonded together, e.g. via their respective $R_1$ substituents (Formula A) or via their $R_6$ or $R_7$ substituents (Formula B) or via a spacer group;

$R_{10}$, $R_{11}$, $R_{12}$, $R_{13}$, $R_{14}$, $R_{15}$ and $R_{16}$ are independently selected from hydrogen or an aromatic substituent as defined herein; and $X^-$ is an anionic moiety, such as halogen (e.g. $Cl^-$, $Br^-$ or $I^-$), tosylate or mesylate.

In a further aspect, the present invention provides compounds represented by the Formula Bii:

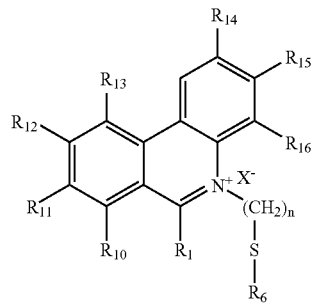

wherein:

n is 2 to 5, more preferably 2-3, and most preferably 2;

$R_1$ is hydrogen or an aromatic substituent;

$R_6$ is hydrogen, a substituent as defined herein or a linking group to form a multimeric compound in which a plurality of compounds represented by Formula A and/or Formula B are covalently bonded together, e.g. via their respective $R_1$, $R_6$ and/or $R_7$ substituents;

$R_{10}$, $R_{11}$, $R_{12}$, $R_{13}$, $R_{14}$, $R_{15}$ and $R_{16}$ are independently selected from hydrogen or an aromatic substituent as defined herein; and $X^-$ is an anionic moiety, such as halogen (e.g. $Cl^-$, $Br^-$ or $I^-$), tosylate or mesylate.

Examples of compounds represented by Formula Bii include the compound 5-[2-(4-methoxy-benzylsulfanyl)-ethyl]-phenanthridinium bromide.

In all of the aspects of the invention, where the $R_2$ and $R_3$ and/or $R_4$ and $R_5$ substituents are present, it is preferred that one or both of these pairs of substituents together form an aromatic carbon or heterocyclic ring structure, optionally substituted with one or more aromatic substituents as defined herein.

In a further aspect, the present invention provides a multimeric compound formed by covalently linking two or more of the compounds as defined above, which may be the same or different. The reaction to produce multimeric compounds according to the present invention may occur spontaneously when compounds of the invention are synthesised or via an additional reaction. Conveniently, compounds of Formula A can be linked via the $R_1$ substituent and compounds represented by Formula B can be linked via the $R_6$ and/or $R_7$ substituents. Where the compounds are linked via the $R_6$ and $R_7$ substituents, the resulting linkage can form a cycloalkyl group. By way of example, the compounds defined herein can be used to form dimers, trimer, tetramers or higher order multimers, e.g. by the use of one or more spacer groups. Examples of linker groups include $C_{1-7}$ alk-di-yl bonded to another group of Formula A or B in place of $R_1$ thereof; piperazin-di-yl bonded to another group of Formula A or B in place of $R_1$ thereof; (N,N-$C_{1-6}$ dialkylene) $C_{1-7}$ alkylene amine bonded to two other groups of Formula A or B in place of $R_1$ thereof; or cyclo ($C_{4-8}$) alk-tri-yl bonded to two other groups of Formula A or B in place of $R_3$ thereof.

In the present invention, spacer groups provide a skeleton on which compounds of Formula A and/or B can be bonded. Spacer groups can be used to form multimeric compounds having 2 or more, 3 or more, 4 or more, 5 or more, 10 or more, 20 or more, 50 or more, or 100 or more compounds represented by Formula A or B linked via one or more spacer groups. Examples of spacer groups are polyamine compounds, examples of which are shown in FIG. 2, which comprise an alkyl chain having a plurality of functional groups such as amines for reacting with the compounds of Formula A an/or B as described herein. As well as the compounds shown in FIG. 2 in which compounds of the present invention are grafted onto one spacer, it is possible to envisage using a plurality of spacers bridged by compounds of the present invention. This can allow the synthesis of multimers having molecular weights of more than about 10 kDa, more than about 20 kDa, more than about 30 kDa to a molecular weight range of about 30 to about 60 K Daltons, e.g. for a 100-mer.

Examples of multmeric compounds include:

Dimers:
Ethylene diamine derivative with two groups of Formula A.
Hydroxylamine derivative with two groups of Formula B.
Piperazine derivative with two groups of Formula B.
DIP dimer derived from the spacer N1-(2-Amino-ethyl)-ethane-1,2-diamine
DIP dimer derived from the spacer 2-Amino-1-[4-(2-amino-acetyl)-piperazin-1-yl]-ethanone
DIP dimer derived from the spacer 2-[4-(2-Amino-ethyl)-piperazin-1-yl]-ethylamine
Phenanthridinium dimer derived from the spacer 2-[4-(2-Amino-ethyl)-piperazin-1-yl]-ethylamine Trimers:
Tris (2-aminoethylamine) derivatives with three groups of Formula A
Cis-triaminocyclohexane derivatives with three groups of Formula A.
2-Amino-1-[5,9-bis-(2-amino-acetyl)-1,5,9triaza-cyclododec-1-yl]-ethanone derivative with three groups of Formula A.
2-[5,9-Bis-(2-amino-ethyl)-1,5,9triaza-cyclododec-1-yl]-ethylamine derivative with three groups of Formula A.
1,5,9-triaza-cyclododecane derivative with three groups of Formula B.
DIP trimer derived from the spacer 2-Amino-1-[5,9-bis-(2-amino-acetyl)-1,5,9triaza-cyclododec-1-yl]-ethanone.
DIP trimer derived from the spacer Cyclohexane-1,3,5-triamine
Phenanthridinium trimer derived from the spacer 2-[5,9-Bis-(2-amino-ethyl)-1,5,9triaza-cyclododec-1-yl]-ethylamine Tetramers:
Tetrakis-(6-amino-hexyl)-ammonium bromide derivative with four groups of Formula A.

In other aspects, the present invention provides methods for synthesising the compounds of the invention. The inventors have also elucidated the mechanism of these reactions which are unprecedented. The reaction to form compounds of Formula A proceeds via three coupled spontaneous reaction steps in a kind of cascade reaction. The sequence of the cascade is: alpha addition, cyclisation followed by an in-situ oxidation step. In one embodiment of the invention (Method A), the in-situ oxidation step occurs via hydride loss and a second equivalent of the precursor that undergoes the initial alpha addition is also consumed as the hydride acceptor under the reaction conditions. This is the first observation of a reaction system that involves an alpha addition step (removing the aromatic nature of the ring) followed by cyclisation and spontaneous re-aromatisation of the ring via hydride loss. In a second embodiment of the method (Method B) for forming compounds represented by Formula A, the in-situ oxidation step uses an oxidizing agent, such as N-bromo-succinimide, to avoid the consumption of an equivalent of the phenanthridinium starting material. Alternatively, method B employs a biphasic solution of water/ethyl acetate and allows the isolation of the non-oxidized newly formed 5 or 6-membered ring in the organic layer whereas the excess of base and its HBr salt is eliminated by an aqueous wash. The non-oxidised intermediate in the ethyl acetate can then be oxidized by NBS to form the final molecule.

Advantageously, a buffer can be used (e.g. $NaHCO_3$ buffer) to avoid the pH of the reaction rising too much whereby a competitive reaction can take place in which hydroxide alpha addition leads to a pseudo-base adduct. Therefore preferably, the pH of the reaction is less that about 10, and more preferably is less than about 9.

For primary amines, this second method B is much more advantageous than the first one. Nevertheless, the first Method A is generally preferred for the formation of dimers, trimers and multimers because, for solubility reasons, DMF is more appropriate. Method A is also better for the formation of [5-(2-amino-alkyl)-phenanthridiniums via the use of secondary amines.

Accordingly, the synthetic methods disclosed herein provide a strategy for the synthesis of the compounds of the invention. In the syntheses illustrated herein, the reaction of a primary amine is used to produce derivatives of [2,3-dihydro-1H-imidazo[1,2-f]phenanthridin-4-ylium bromide] or the reaction of a secondary amine is used to produce derivatives of [5-(2-amino-ethyl)-phenanthridinium. However, the reactions disclosed herein are general and can be extended to other heterocyclic aromatic moieties containing a ring nitrogen and at least one adjacent alpha hydrogen. Furthermore, the reactions are extremely easy to perform as isolating a pure final product simply requires a filtration and a washing procedure to afford product in high yield.

Accordingly, in a further aspect, the present invention provides a method of synthesising a heterocyclic aromatic cationic compound with an additional ring, the method comprising reacting a heterocyclic aromatic cationic compound comprising a ring nitrogen and at least one alpha hydrogen atom with a substituted or unsubstituted primary amine, a sulphate or a hydroxide, wherein the primary amine, sulphate or hydroxide reacts with the heterocylic aromatic compound by alpha addition, cyclisation and an oxidation step thereby providing the heterocyclic aromatic compound with an additional ring. In preferred embodiments, the ring produced in this reaction is five membered. In a preferred embodiment, the heterocyclic aromatic starting material is the 2-bromo-ethyl-phenanthridinium, which reacts with a primary amine to yield a 2,3-Dihydro-1H-imidazo[1,2-f]phenanthridin-4-ylium bromide derivative.

The method can be used for the production of 5 and 6-membered rings and to produce thiazole and oxazoles as well as phenanthridinium compounds by using a sulphate or a hydroxide respectively. The Methods A and B described herein are particularly advantageous as they involve an addition and a cyclisation followed by an aromatisation process that involves one equivalent of the starting material as an oxidizing agent (Method A) or a external oxidizing agent like NBS (Method B). In preferred embodiments, this has the particular advantage that the reaction can proceed in one pot. While the application of this new chemistry to the production of phenanthridinium compounds in which the b ring is extended is preferred, the reaction is equally applicable to the extension of other heteroaromatic compounds such as quinolines, isoquinolines, quinazolines or pyridines.

In one embodiment, the method is for making a compound represented by Formula A and comprises:
  reacting a heterocyclic aromatic compound represented by the Formula A':

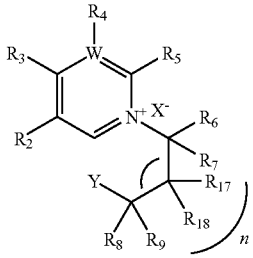

wherein Y is a leaving group and n and the remaining substituents are as defined above;
with a primary amine represented by the formula:

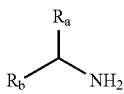

wherein the $R_a$—C—$R_b$ substituents of the primary amine forms the group $R_a$ in the final compound;
the primary amine reacting with the phenanthridinium compounds of Formula A' by addition, cyclisation and oxidation to produce a compound represented by Formula A.

In further embodiments, the method of making a compound represented by Formula Ai or Aii, the method comprising:
  reacting a heterocyclic aromatic compound represented by the Formula Ai' or Aii' respectively:

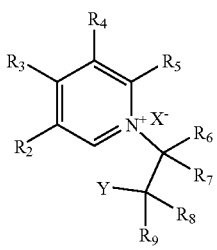

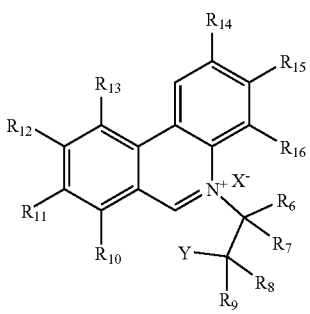

wherein Y is a leaving group and the remaining substituents are as defined above;

with a primary amine represented by the formula:

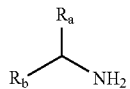

wherein the $R_a$—C—$R_b$ substituents of the primary amine forms the group $R_1$ in the final compound;
the primary amine reacting with the phenanthridinium compounds of Formula Ai' by addition, cyclisation and oxidation to produce a compound represented by Formula Ai.

Examples of primary amines that can be reacted with compounds of general Formula A include:
  Aliphatic primary amines, which (1) have no substituents in the alpha position (e.g. ammonia), (2) have a primary carbon in the alpha position (e.g. methyl amine), (3) have a secondary carbon in the alpha position (such as an alkyl amine), (4) have a tertiary carbon in the alpha position (such as isopropylamine or amino acids other than glycine), or (5) are or derive from an amino acid.
  Aromatic amines, and preferably aromatic amines without bulky beta substituents such as naphthalen-1-ylamine or anthracen-9-ylamine.
  A hydrochloride of an aliphatic and aromatic amine are described above.
  The primary amines preferably do not include amines having a quaternary carbon on its alpha position such as isobutylamine or amines having a carbonyl in the alpha position such as acetamide.

In a further aspect, the present invention provides a method of making compounds represented by Formula B, the method comprising:
  reacting a heterocyclic aromatic compound represented by the Formula B':

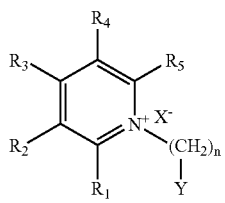

wherein Y is a leaving group and the remaining substituents are as defined above;
with a secondary amine represented by the Formula:

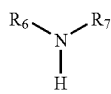

the secondary amine reacting with the compound of Formula B' to produce a compound represented by Formula B.

Without wishing to be bound by a particular theory, the present inventors believe that the reaction to produce compounds represented by Formula B comprises nucleophilic attack of secondary amine on the compound of Formula B' to undergo alpha addition to the heteroaromatic ring, attack of the lone pair of the newly formed tertiary amine onto the carbon linked to the leaving group Y, thereby causing this quaternary ammonium group to leave by attack of the lone pair on the heteroaromatic ring N to cause the alpha C—N bond to break and provide the product, with rearomatization being the driving force.

In a further aspect, the present invention provides a method of making compounds represented by Formula Bi, the method comprising:
reacting a heterocyclic aromatic compound represented by the Formula Bi':

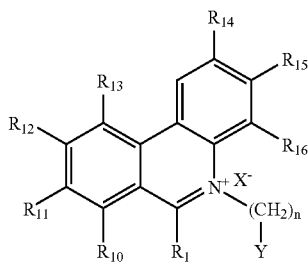

wherein Y is a leaving group and the remaining substituents are as defined above;
with a secondary amine represented by the formula:

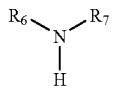

the secondary amine reacting with the compound of Formula Bi' by to produce a compound represented by Formula Bi.

In a further aspect, the present invention provides a method of making compounds represented by Formula Bii, the method comprising:
reacting a heterocyclic aromatic compound represented by the Formula Bii':

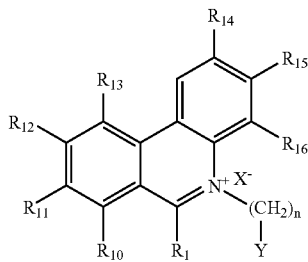

with a sulphur containing compound such as substituted or unsubstituted thiol to produce a compound represented by Formula Bii, e.g. as disclosed in the examples below.

In the methods disclosed herein for the production of compounds of the present invention represented by Formula A or B, the method may comprise the additional step of forming a multimeric compound.

Structure B is also formed through the one-pot three step mechanism. Some secondary amine substitutions on 2-bromo-ethyl-pyridinium salt derivatives other than 2-Bromo-ethyl-phenanthridinium have been described already in the literature through an $SN_2$ mechanism. However, without wishing to be bound by any particular theory, the present inventors believe that this $SN_2$ mechanism is wrong and that the reaction proceeds via a non-$SN_2$, non-$SN_1$ mechanism as described herein.

In a further aspect, the present invention provides a composition comprising one or more compounds as defined herein.

In a further aspect, the present invention provides a compound as defined herein for use in a method of medical treatment.

In a further aspect, the present invention provides the use of the compounds as defined herein as DNA cross linking agents, DNA binding agents, telomere binding agents, biological probes or diagnostic probes.

In a further aspect the present invention provides the use of the compounds defined herein for the preparation of a medicament for the treatment of a condition treatable by an anti-cancer agent, an anti-inflammatory agent, as antiprotozoal agent, or a topoisomerase inhibitor.

In a further aspect, the present invention provides the use of a compound as defined herein as a synthetic agent, by way of example, as a reducing agent, a chiral reducing reagent (that is a substance that is capable of reducing an achiral substrate to selectively produce more of a given enantiomer over another), an amine protecting group, a phase transfer catalyst, a chiral resolving agent for purification or crystallisation.

In a further aspect, the present invention provides the use of a compound as defined herein as an electronic material, a photochemically active agent or sensor or as molecular switching device.

Other areas of use of the compounds may include the use of these new frameworks in combinatorial chemistry to form biologically active components that are active in areas other than DNA binding and these may be, for instance, dopamine inhibitors, NADH mimics and as a general heterocyclic fragment for drug design to cover the area of alkaloid chemistry.

Other preferred areas of application of the compounds may include their use as DNA binders as anti cancer drugs and other drugs that need to target DNA, ageing moderators, DNA binding tools for molecular biology, gene expression, DNA sensors and spectroscopically active DNA binding and bending sensors, new heterocylic frameworks for drug discovery, dopamine drugs, NADH-based drugs, spectroscopically active binding molecules.

To elaborate on the use of the aforementioned compounds as genomic probes and diagnostic agents, given the ease of the reaction, and the number of DNA intercalating units that may be linked together using this technology, it is possible to produce libraries of tethered units that can be used to detect a given gene etc, see FIG. 2.

In this way, an infinitely variable library of DIP-based molecules can be produced and supported on a gold surface to perform Surface Plasmon Resonance studies (SPR). Therefore, DIP-based (formula A) or extended heterocylic cations (formula B) molecules can be used as biosensor to identify binding events with DNA flowing across the surface. This or a related technology can be used to provide specific gene targeting using a molecular library generated using the molecules of the type A or B.

Embodiments of the invention will now be described in more detail, by way of example and not limitation, with reference to the accompanying figures.

DETAILED DESCRIPTION

Abbreviations

Figure 1:
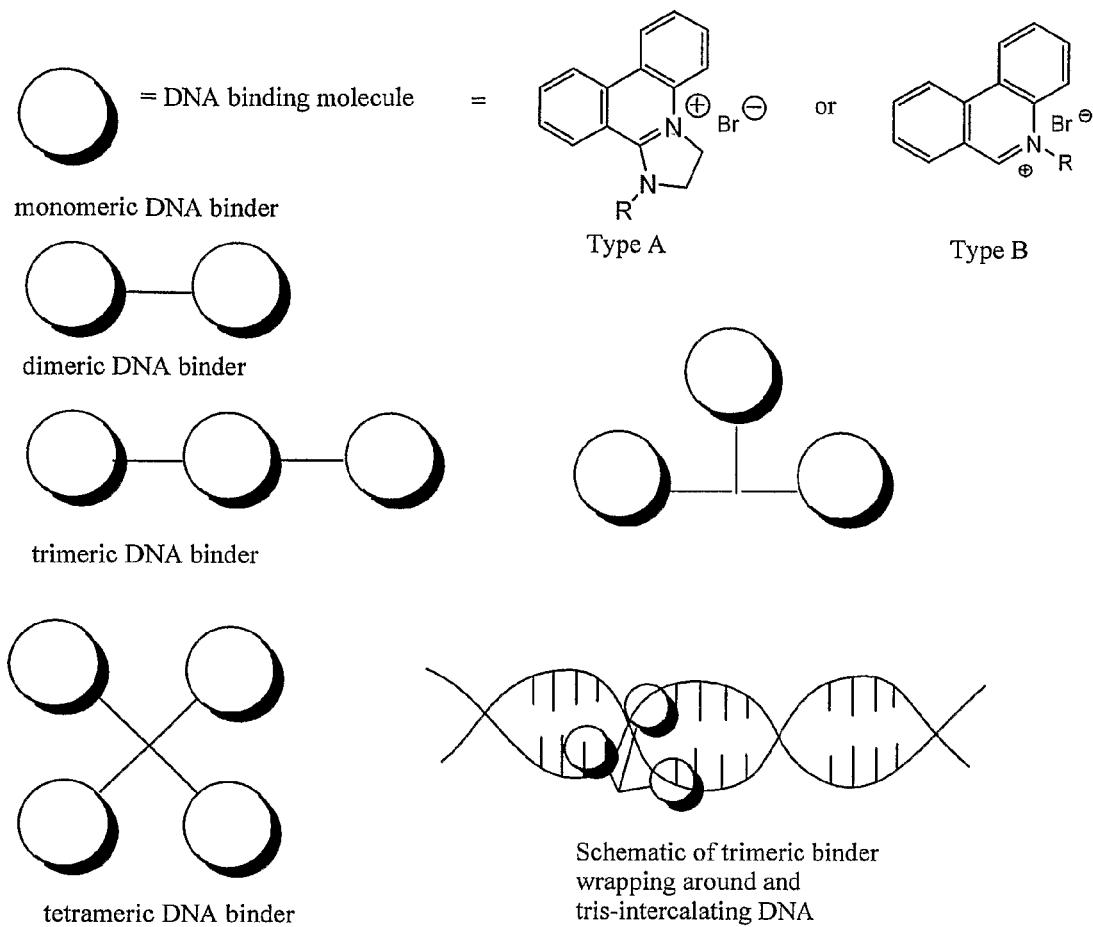
FIG. 1 shows a schematic diagram indicating how the compounds of the present invention, including dimers, trimer and tetramers are constructed and how they might intercalate with DNA.
Figure 2:
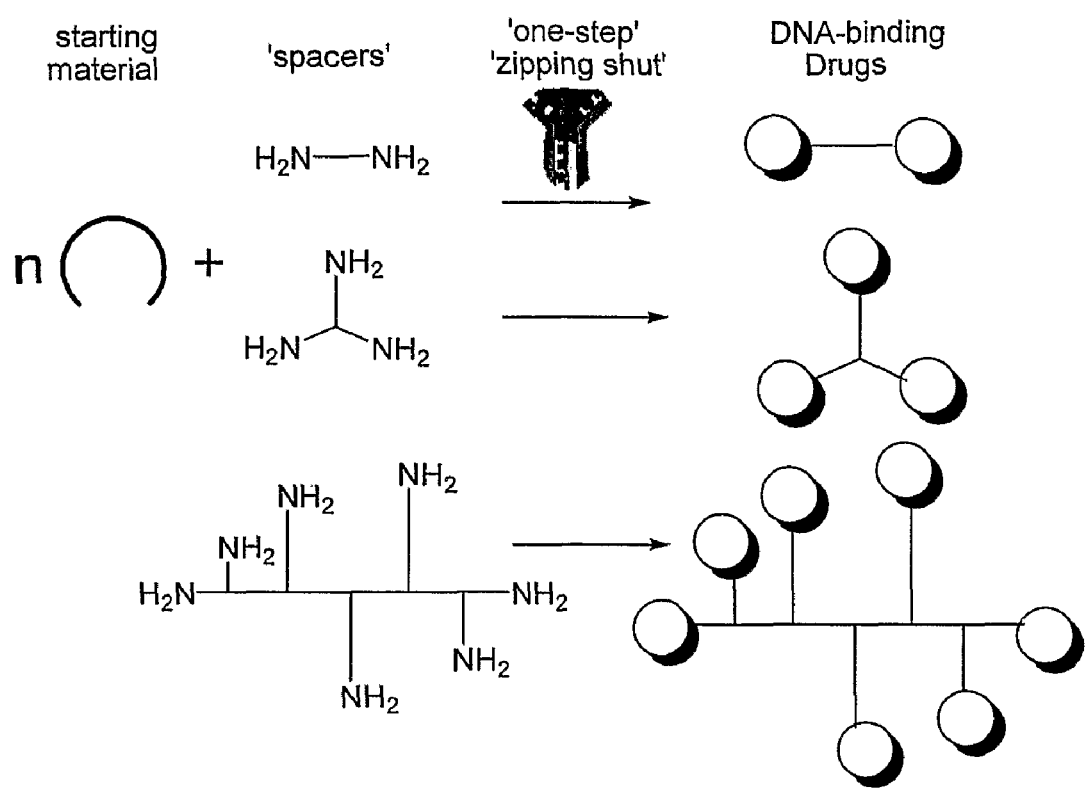
FIG. 2 shows a schematic diagram showing how multimeric compounds can be formed from compounds of the present invention using spacer groups.
Figure 3:
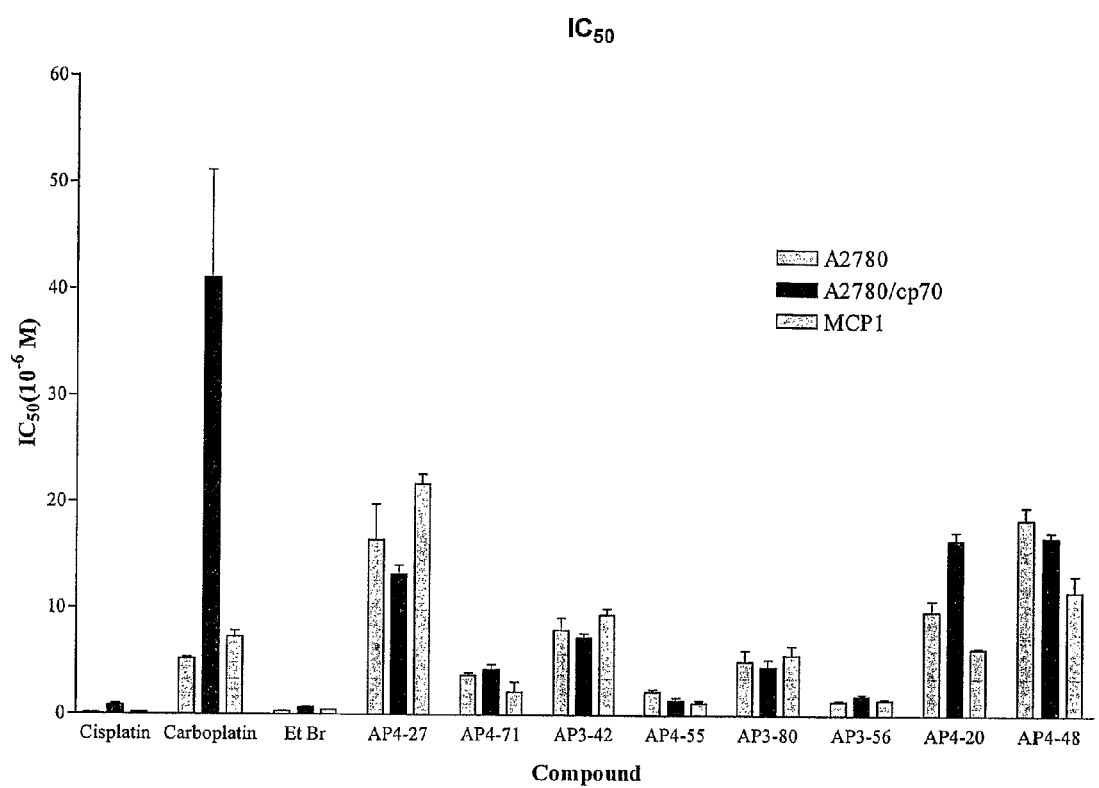
FIG. 3 shows a plot of IC50 values when compounds according to the present invention and cisplatin and carboplatin are contacted with three different tumour cell lines (A2780, A2780/cp70 and MCP1).
Figure 4:
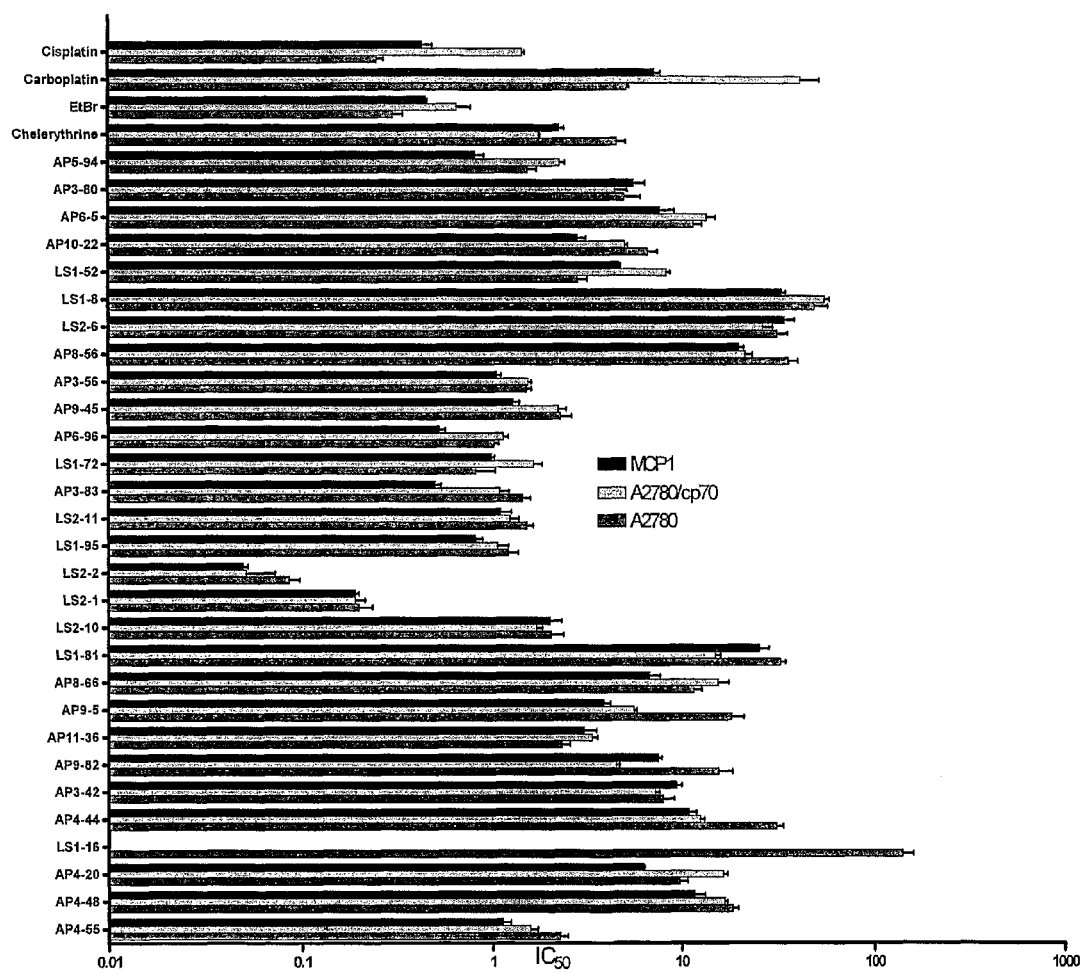
FIG. 4 shows the effect of drugs as the logarithm of their $IC_{50}$ (μM) on the three cell lines: cisplatin-sensitive cell line A2780 and cisplatin-resistant cell lines A2780/cp70 and MCP1 respectively.

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biph), benzyl (Bn), naphthyl (naph), methoxy (MeO), ethoxy (EtO), benzoyl (Bz), and acetyl (Ac), and triethylamine (TEA).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

General Substituents

As indicated herein, the compounds of the present invention may be unsubstituted or substituted by one or more functional groups. Unless otherwise specified, the term "substituted" means a parent group which bears one or more substituents. The term "substituent" is used herein in the conventional sense and refers to a chemical moiety which is covalently attached to, appended to, or if appropriate, fused to, a parent group. A wide variety of substituents are well known in the art, and methods for their formation and introduction into a variety of parent groups are also well known.

In the present invention, "aromatic substituent" as defined herein are independently selected from hydrogen, —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, -Ph, ether (e.g., $C_{1-7}$alkoxy); ester; amido; amino; and, $C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl).

In the present invention, "substituent" as defined herein are independently selected from hydrogen, halo; hydroxy; oxo; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl (including $C_{5-6}$heterocyclyl) or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl), and especially $C_{5-6}$aryl).

In one preferred embodiment, the substituent(s) are independently selected from:
—F, —Cl, —Br and —I;
=O
—OH;
—OMe, —OEt, —O(tBu) and —OCH$_2$Ph;
—SH;
—SMe, —SEt, —S(tBu) and —SCH$_2$Ph;
—C(=O)H;
—C(=O)Me, —C(=O)Et, —C(=O) (tBu) and —C(=O)Ph;
—C(=O)OH;
—C(=O)OMe, —C(=O)OEt and —C(=O)O(tBu);
—C(=O)NH$_2$, —C(=O)NHMe, —C(=O)NMe$_2$ and —C(=O)NHEt;
—NHC(=O)Me, —NHC(=O)Et, —NHC(=O)Ph, succinimidyl and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$ and —N(tBu)$_2$;
—CN;
—NO$_2$;
-Me, -Et, -nPr, -iPr, -nBu and -tBu;
—CF$_3$, —CHF$_2$, —CH$_2$F, —CCl$_3$, —CBr$_3$, —CH$_2$CH$_2$F, —CH$_2$CHF$_2$ and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$ and —OCH$_2$CF$_3$;
—CH$_2$OH, —CH$_2$CH$_2$OH and —CH(OH)CH$_2$OH;
—CH$_2$NH$_2$, —CH$_2$CH$_2$NH$_2$ and —CH$_2$CH$_2$NMe$_2$; and,
substituted or unsubstituted phenyl.

For phenyl substituents, if the phenyl group has less than the full complement of substituents, they may be arranged in any combination. For example, if the phenyl group has a single substituent other than hydrogen, it may be in the 2-, 3-, or 4-position. Similarly, if the phenyl group has two substituents other than hydrogen, they may be in the 2,3-, 2,4-, 2,5-, 2,6-, 3,4-, or 3,5-positions. If the phenyl group has three substituents other than hydrogen, they may be in, for example, the 2,3,4-, 2,3,5-, 2,3,6-, 2,4,5-, 2,5,6-, or 3,4,5-positions. If the phenyl group has four substituents other than hydrogen, they may be in, for example, the 3,4,5,6-, 2,4,5,6-, 2,3,5,6-, 2,3,4,6-, or 2,3,4,5-positions.

In one preferred embodiment, the substituent(s), often referred to herein as $R_1$ to $R_{17}$, are independently selected from:
—OH;
=O
—OMe, —OEt, —O(tBu) and —OCH$_2$Ph;
—C(=O)OMe, —C(=O)OEt and —C(=O)O(tBu);
—C(=O)NH$_2$, —C(=O)NHMe, —C(=O)NMe$_2$ and —C(=O)NHEt;
—NH$_2$, —NHMe, —NHEt, —NH(iPr)-NH(nPr), —NMe$_2$, —NEt$_2$, —N(iPr)$_2$, —N(nPr)$_2$, —N(nBu)$_2$ and —N(tBu)$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$CH$_2$OH, and —CH(OH)CH$_2$OH; and,
—CH$_2$NH$_2$, —CH$_2$CH$_2$NH$_2$ and —CH$_2$CH$_2$NMe$_2$.

Alternative Forms of Compounds

The compounds of the invention may be derivatised in various ways. As used herein "derivatives" of the compounds includes well known ionic, salt, solvate and protected forms of the compounds or their substituents mentioned herein. For example, a reference to carboxylic acid (—COOH) also includes the anionic (carboxylate) form (—COO$^-$), a salt or solvate thereof, as well as conventional protected forms.

Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

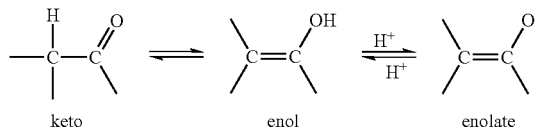

keto        enol        enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

It may be convenient or desirable to prepare, purify, and/or handle a corresponding salt of the active compound, for example, a pharmaceutically-acceptable salt. Examples of pharmaceutically acceptable salts are discussed in Berge et al, Pharmaceutically Acceptable Salts, J. Pharm. Sci., Vol. 66: 1-19, 1977.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts; 3rd Edition; John Wiley and Sons, 1999).

A wide variety of such "protecting", "blocking" or "masking" methods are widely used and well known in organic synthesis. For example, a compound which has two non-equivalent reactive functional groups, both of which would be reactive under specified conditions, may be derivatized to render one of the functional groups "protected" and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_{15}$, —NH-Bpoc), as a 9-fluorenylmethoxy, amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug" as used herein, means a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: C$_{1-7}$alkyl (e.g., -Me, -Et, -nPr, -iPr, -nBu, -sBu, -iBu, -tBu); C$_{1-7}$aminoalkyl (e.g., aminoethyl; 2-(N,N-diethylamino)ethyl; 2-(4-morpholino)ethyl); and acyloxy-C$_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy) carbonyloxyethyl; (4-tetrahydropyranyl) carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Solvents

Solvents may conveniently be classified according to one or more of their physical or chemical properties. For example, solvents may be classified according to their polarity, that is, their permanent dipole moment. Examples of highly polar solvents include dimethylsulfoxide (DMSO), dimethylformamide (DMF), dimethylacetamide, and acetonitrile (ACN). Examples of moderately polar solvents include acetone, methanol, tetrahydrofuran (THF), ethyl acetate (AcOEt), and water. Examples of relatively non-polar solvents include diethyl ether, chloroform, and dichloromethane (DCM). Examples of non-polar and virtually non-polar solvents include alkanes, benzene, toluene, and carbon tetrachloride.

Solvents may also be classified as "protic" or "aprotic" according to their proton-exchange properties. Protic solvents accept and/or donate protons. Examples of protic solvents include water, alcohols, carboxylic acids (e.g., acetic acid), and amines (e.g., ammonia, pyridine). Aprotic solvents neither accept nor donate protons. Examples of aprotic solvents include carbon tetrachloride, chloroform, dichloromethane (DCM), acetonitrile (ACN), ethyl acetate (AcOEt), dimethylacetamide, tetrahydrofuran (THF), dimethylformamide (DMF), toluene, benzene, acetone, ethers (e.g., diethyl ether), alkanes (e.g., hexane), dimethylsulfoxide (DMSO), sulfur dioxide, hexamethylphosphoramide (HMPA), and, tetramethylurea. Amphoteric solvents, such as water, are capable of both accepting and donating protons.

Solvents may also be classified as "organic" or "inorganic" according to their chemical composition. Conventionally, organic solvents comprise, at least, carbon atoms, while inorganic solvents do not. Examples of inorganic solvents include water, ammonia, and sulfur dioxide. Examples of organic solvent include carbon tetrachloride (CCl$_4$); chloroform (CHCl$_3$); dichloromethane (DMC, CH$_2$Cl$_2$); acetonitrile (ACN); ethyl acetate (AcOEt); ethanol (EtOH); methanol (MeOH); dimethylacetamide; tetrahydrofuran (THF); dimethylformamide (DMF); toluene; benzene; acetone; ethers (e.g., diethyl ether); alkanes (e.g., hexane); water; liquid ammonia; dimethylsulfoxide (DMSO); sulfur dioxide, hexamethylphosphoramide (HMPA); tetramethylurea; tetramethylene sulfone (sulfolane).

Applications of the Compounds

The compounds of the present invention may be used in the field of biology as a DNA cross linking agent, a DNA binding agent, a telomere binding agent, a drug such as an anti-cancer drug, a diagnostic probe, a probe for molecular biology, an anti-inflammatory agent, an antiprotozoal agent, a topoisomerase inhibitor and/or a bioactive drug or cofactor.

The compounds of the present invention may also be used as synthetic agents, by way of example, as reducing agents, chiral reagents, chiral reducing agents, amine protecting groups or phase transfer catalysts.

The compounds of the present invention may be used as in the production of electronic materials, photochemically active agents and sensors, or as molecular switching devices.

DNA Binding

The concepts behind the design of these molecules for DNA binding is given in FIG. 1. DNA intercalation occurs by insertion of a flat aromatic system in between two sets of DNA base pairs, see for example the paper 'Intercalators as Anticancer Drugs' by M. F. Brana et al in Current Pharmaceutical Design, 2001, 7, 1745.

Biology

Generally, preferred compounds of the present invention are water soluble molecules, but are sufficiently lipophilic to be capable of crossing the plasmic membrane and nuclear membrane of the cells. They also preferably have high affinities for DNA. These properties mean that the compounds may find use in pharmaceuticals. To investigate this, examples of compounds of the present invention have been tested in cell cytotoxicity assays, comparing their properties to cisplatin and carboplatin, two known cross-linking agents used in the treatment of cancer.

Compounds were tested in a growth assay with a 24 hours drug exposure and a 3 day recovery period. Cell lines used were human ovarian tumour cell line A2780 and 2 Cisplatin resistant derivatives cell lines A27080/cp70 and MCP1. $IC_{50}$ is the concentration of drug required to reduce the surviving cell number to 50% of that of the control untreated cells. Results are from one experiment and are the mean±SEM of the triplicate plates.

The compounds of the invention were found to be cytotoxic to non-resistant and resistant cisplatin cell lines with $IC_{50}$'s between those of cisplatin and carboplatin. While not wishing to be bound by any particular theory, the present inventors believe that the high affinity of the compounds for DNA means that the cytotoxic effect of the compounds is more DNA targeted than cisplatin or carboplatin which do not have any intrinsic DNA affinity.

Preferred compounds of the invention are stable molecules and are resistant to NADH reduction, unlike some other phenanthridinium derivatives which are not. This may help to increase the bio-availability of the drug since some typical phenanthridinium derivatives have the drawback of being metabolised quickly by reduction reaction in the liver involving NADH. The compounds of the present invention also tend to be more alkali resistant than other phenanthridinium derivatives which have the disadvantage of undertaking easily alpha addition of a hydroxide at physiological pH forming non-planar pseudo-base. The DIP framework is stable up to pH 11 where less than half of the molecules undertake the alpha addition of a hydroxide. With typical phenanthridinium derivatives bearing one hydrogen on their alpha position, more than half of the molecules undertake a pseudo-base formation at pH above 8.5. By way of illustration, this is based on spectroscopic measurement where pKa(OH) of DIP frameworks were found above 11, whereas pKa(OH) of the reference 5-methyl-phenanthridinium bromide were found below 8.5. The DIP framework has therefore the advantage of keeping its planarity at physiological pH to interact with DNA. The other phenanthridinium derivatives undertake to some extend the pseudo-base formation at physiological pH, disturbing the planarity of the molecule and therefore loosing part of their affinity for the DNA.

The compounds of the present invention are generally highly stable to base and acid. This means that the compounds could be suitable for oral administration.

Without wishing to be bound by any particular theory, the present inventors believe that the compounds of the invention can be modified and tuned so that they could be, for instance, subject to reduction or pseudo-base formation upon DNA intercalation. The stability of the DIP framework could be controlled by finding the right substituent so that the molecule could be switched in the DNA duplex to an inactive form (this is not limited to but may include reduction or pseudo base formation). This means that the drug will be particularly effective in cells that are undergoing fast turnover i.e. cancer cells but in slow growing cells, like most normal cells, the drug will be much less toxic. Thus, the DIP framework has the possibility to be tuned to be more toxic in fast growing cells like cancer cells, because the cells would not have enough time to undertake the metabolisation process.

Finally, the DIP framework has a positive charge which is easily delocalized between its two nitrogen atoms. The molecule could therefore adjust the position of its charge to increase the DNA binding, notably the ionic interaction between its cationic ammonium and the anionic phosphate backbone of the DNA duplex.

In summary, the compounds of the present invention generally may have a range of properties that make them suitable for use as pharmaceuticals.

1. The compounds are typically amphiphilic, with their lipophilic nature being useful for crossing cell membranes, whereas their hydrophilic character is important for the solubilisation of the drug in the blood stream.
2. Experiments also indicate that the compounds possess a high DNA affinity in DNA melting point experiments and ITC (Isothermal Titration Calorimetry).
3. The cytotoxicity of the majority of a group of exemplified lead compounds is between Cisplatin and Carboplatin, as shown in the experiments reported herein. In the experiments, these compounds demonstrated a tendency to be more active on Cisplatin-resistant cell lines compared to Cisplatin-sensitive cell lines. Some particular DIP derivatives were found to be much more active than the clinical agent Carboplatin on Cisplatin-resistant cell line (up to a 790 fold difference).
4. The DNA affinity properties of the compounds of the present invention may mean that their cytotoxicity is more DNA targeted than Cisplatin or Carboplatin which do not have any intrinsic DNA affinity.
5. The DIP framework is more NADH stable than typical phenanthridinium derivative. This could lead to a better bioavailability.
6. Compounds based on the DIP framework may be suitable for oral administration.
7. The DIP framework could offer some drug targeting advantages by tuning the stability of the molecule so that normal cells would have enough time to undertake the destructive metabolisation process, whereas the cancerous fast growing cells would not.
8. The DIP framework could position its positive charge on one or the other of its nitrogen atoms through conjugation in order to increase the ionic interaction with the DNA.
9. Viscosimetry analysis shows that the DIP framework intercalates between the DNA base pairs.
10. Preliminary animal studies performed on mice bearing a human tumour show with one particular DIP derivative a decrease of the tumour size over the time.

Cytotoxicity Results

The DIP framework was found to have very promising biological activity. Most of the tested derivatives have both affinity for DNA and high cytotoxicity (See following Table and Figure).

DIP cytotoxicity was determined by a tetrazolium dye-based microtitration assay. DNA affinity measurements of DIPs were undertaken using Isothermal Titration Calorimetry (ITC).

TABLE

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/cp70 $IC_{50}$ (μM) | RF1 | MCP1 $IC_{50}$ (μM) | RF2 | Ka $(M^{-1})$ Salmon DNA $(10^4)$ | Ka $(M^{-1})$ Calf DNA $(10^4)$ |
|---|---|---|---|---|---|---|---|
| 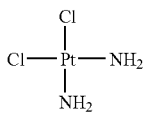 Cisplatin | 0.25 ± 0.02 | 1.46 ± 0.04 | 5.8 | 0.43 ± 0.06 | 1.7 | — | — |
| 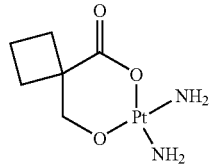 Carboplatin | 5.22 ± 0.14 | 41.1 ± 10.1 | 7.9 | 7.31 ± 0.56 | 1.4 | — | — |
| 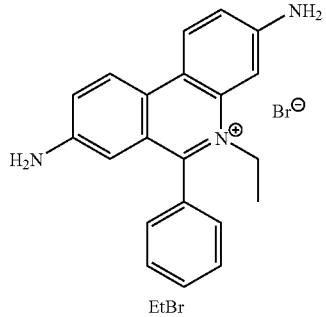 EtBr | 0.3 ± 0.039 | 0.658 ± 0.118 | 2.2 | 0.45 ± 0.008 | 1.5 | 12.9 ± 4533 | 9.31 ± 3353 |
| 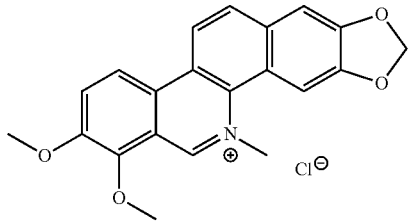 Chelerythrine | 4.63 ± 0.52 | 1.79 ± 0.02 | 0.4 | 2.29 ± 0.15 | 0.5 | — | — |
| 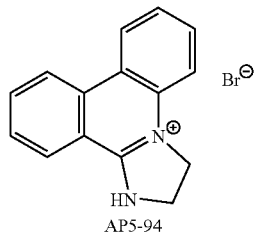 AP5-94 | 1.56 ± 0.18 | 2.30 ± 0.15 | 1.5 | 0.82 ± 0.09 | 0.5 | 2.56 ± 802.6 | 2.06 ± 907 |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/cp70 $IC_{50}$ (μM) | RF1 | MCP1 $IC_{50}$ (μM) | RF2 | Ka ($M^{-1}$) Salmon DNA ($10^4$) | Ka ($M^{-1}$) Calf DNA ($10^4$) |
|---|---|---|---|---|---|---|---|
| 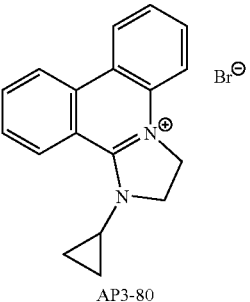 AP3-80 | 5.07 ± 1.06 | 4.54 ± 0.70 | 0.9 | 5.68 ± 0.86 | 1.1 | — | — |
| 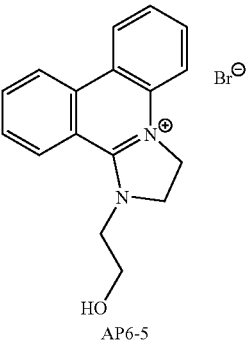 AP6-5 | 11.7 ± 1.2 | 13.7 ± 1.5 | 1.2 | 7.80 ± 1.47 | 0.7 | 1.84 ± 660 | 1.53 ± 838.9 |
| 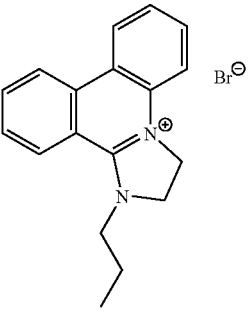 AP10-22 | 6.71 ± 0.86 | 5.11 ± 0.19 | 0.8 | 2.86 ± 0.32 | 0.4 | 3.11 ± 2203 | 3.67 ± 1310 |
| 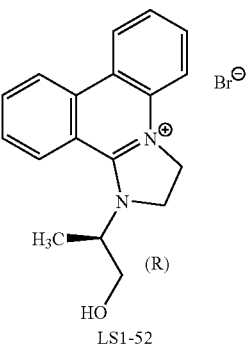 LS1-52 | 2.86 ± 0.37 | 8.43 ± 0.37 | 3 | 4.77 ± 0.09 | 1.7 | 1.73 ± 989.3 | 1.42 ± 785 |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 IC$_{50}$ (μM) | A2780/cp70 IC$_{50}$ (μM) | RF1 | MCP1 IC$_{50}$ (μM) | RF2 | Ka (M$^{-1}$) Salmon DNA (10$^4$) | Ka (M$^{-1}$) Calf DNA (10$^4$) |
|---|---|---|---|---|---|---|---|
| LS1-8 | 48.4 ± 8.5 | 54.9 ± 3.4 | 1.1 | 33.0 ± 1.6 | 0.7 | — | — |
| LS2-6 | 31.2 ± 4.2 | 26.4 ± 3.3 | 0.9 | 34.2 ± 4.3 | 1.1 | — | — |
| AP8-56 | 35.8 ± 4.2 | 21.6 ± 1.80 | 0.6 | 20.0 ± 1.2 | 0.6 | *1 | *1 |
| AP3-56 | 1.53 ± 0.09 | 1.56 ± 0.06 | 1.0 | 1.06 ± 0.06 | 0.7 | 2.89 ± 924.1 | 2.19 ± 644 |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/ cp70 $IC_{50}$ (μM) | RF1 | MCP1 $IC_{50}$ (μM) | RF2 | Ka $(M^{-1})$ Salmon DNA $(10^4)$ | Ka $(M^{-1})$ Calf DNA $(10^4)$ |
|---|---|---|---|---|---|---|---|
| 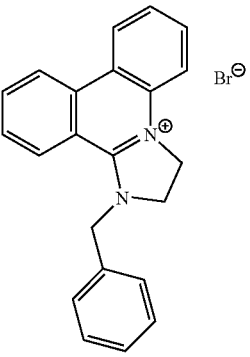<br>AP9-45 | 2.32 ± 0.33 | 2.26 ± 0.23 | 1.0 | 1.29 ± 0.11 | 0.6 | — | — |
| 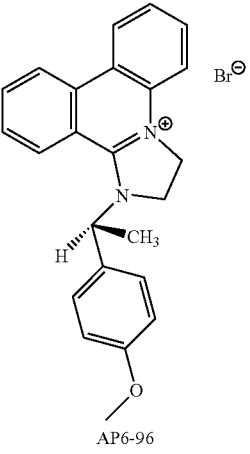<br>AP6-96 | 1.03 ± 0.06 | 1.15 ± 0.07 | 1.1 | 0.53 ± 0.04 | 0.5 | 5.17 ± 1948 | 4.14 ± 2685 |
| 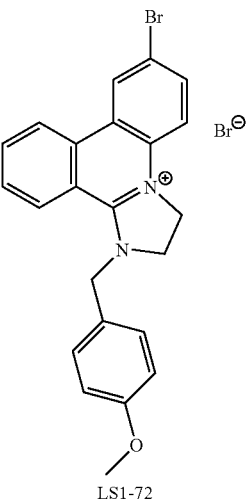<br>LS1-72 | 0.823 ± 0.219 | 1.67 ± 0.18 | 2 | 0.997 ± 0.034 | 1.2 | — | — |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (µM) | A2780/ cp70 $IC_{50}$ (µM) | RF1 | MCP1 $IC_{50}$ (µM) | RF2 | Ka $(M^{-1})$ Salmon DNA $(10^4)$ | Ka $(M^{-1})$ Calf DNA $(10^4)$ |
|---|---|---|---|---|---|---|---|
| AP3-83 | 1.45 ± 0.15 | 1.10 ± 0.13 | 0.8 | 0.50 ± 0.04 | 0.3 | 3.73 ± 1827 | 3.46 ± 1726 |
| LS2-11 | 1.54 ± 0.12 | 1.25 ± 0.14 | 0.8 | 1.11 ± 0.16 | 0.7 | — | — |
| LS1-95 | 1.22 ± 016 | 1.07 ± 0.15 | 0.9 | 0.82 ± 0.07 | 0.7 | — | — |
| LS2-1 | 0.087 ± 0.011 | 0.05 ± 0.021 | 0.6 | 0.05 ± 0.003 | 0.6 | — | — |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/cp70 $IC_{50}$ (μM) | RF1 | MCP1 $IC_{50}$ (μM) | RF2 | Ka ($M^{-1}$) Salmon DNA ($10^4$) | Ka ($M^{-1}$) Calf DNA ($10^4$) |
|---|---|---|---|---|---|---|---|
| LS2-2 | 0.198 ± 0.036 | 0.19 ± 0.024 | 1 | 0.191 ± 0.008 | 1 | — | — |
| LS2-10 | 2.06 ± 0.34 | 1.73 ± 0.12 | 0.8 | 2.03 ± 0.31 | 1 | — | — |
| LS1-81 | 32.4 ± 2 | 15.1 ± 0.9 | 0.5 | 25.4 ± 2.9 | 0.8 | — | — |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/ cp70 $IC_{50}$ (μM) | RF1 | MCP1 $IC_{50}$ (μM) | RF2 | Ka ($M^{-1}$) Salmon DNA ($10^4$) | Ka ($M^{-1}$) Calf DNA ($10^4$) |
|---|---|---|---|---|---|---|---|
| AP8-66 | 11.7 ± 1.1 | 15.6 ± 2.1 | 1.3 | 6.84 ± 0.89 | 0.6 | — | — |
| AP9-5 | 18.3 ± 2.8 | 5.65 ± 0.20 | 0.3 | 3.94 ± 0.32 | 0.2 | — | — |

TABLE-continued
Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)
| Structure | A2780 $IC_{50}$ (μM) | A2780/cp70 $IC_{50}$ (μM) | RF1 | MCP1 $IC_{50}$ (μM) | RF2 | Ka ($M^{-1}$) Salmon DNA ($10^4$) | Ka ($M^{-1}$) Calf DNA ($10^4$) |
|---|---|---|---|---|---|---|---|
| AP11-36 | 2.34 ± 0.25 | 3.40 ± 0.23 | 1.5 | 3.07 ± 0.52 | 1.3 | — | — |
| AP9-82 | 15.63 ± 2.76 | 4.57 ± 0.18 | 0.3 | 7.59 ± 0.32 | 0.5 | — | — |
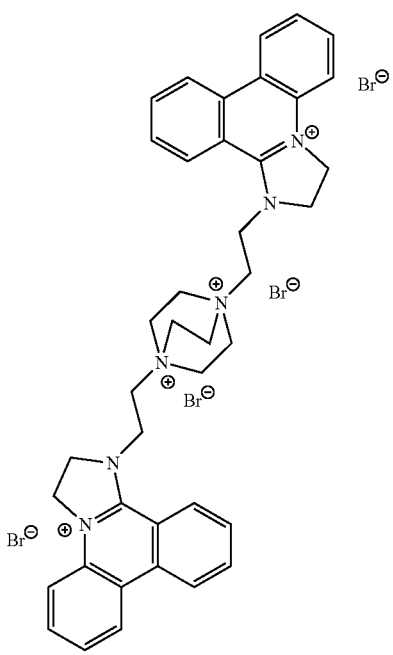
AP11-36
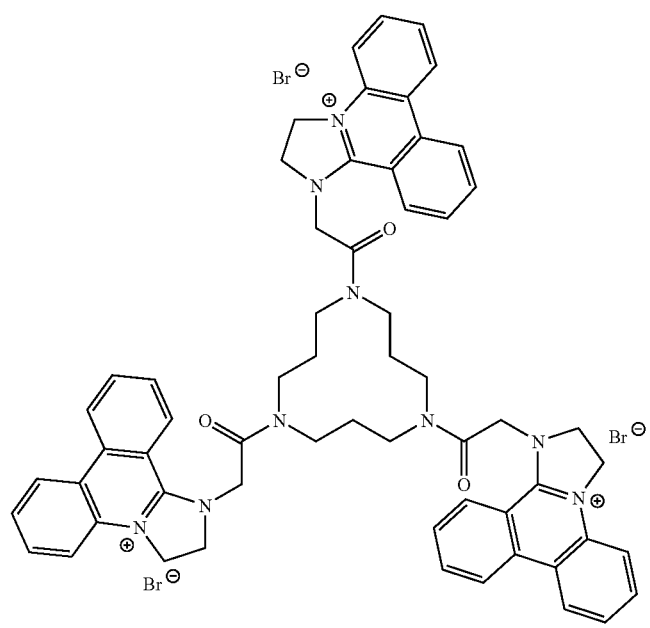
AP9-82

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/ cp70 $IC_{50}$ (μM) | RF1 | MCP1 $IC_{50}$ (μM) | RF2 | Ka $(M^{-1})$ Salmon DNA $(10^4)$ | Ka $(M^{-1})$ Calf DNA $(10^4)$ |
|---|---|---|---|---|---|---|---|
| AP3-42 | 8.02 ± 1.14 | 7.29 ± 0.38 | 0.9 | 9.44 ± 0.58 | 1.2 | — | — |
| AP4-44 | 30.9 ± 2.5 | 12.6 ± 0.6 | 0.4 | 11.0 ± 1.0 | 0.4 | *1 | *1 |
| LS1-16 | 141.5 ± 19.1 | >10$^{-4}$ | | >10$^{-4}$ | | — | — |
| AP4-20 | 9.77 ± 1.04 | 16.51 ± 0.80 | 1.7 | 6.30 ± 0.09 | 0.6 | — | — |

TABLE-continued

Structure with corresponding LogP, cytotoxicity and DNA affinity. $RF_1$ and $RF_2$ are the rapport of the $IC_{50}$ between cisplatin-sensitive cell line A2780 and cisplatin-resistant cell lines A2780/cp70 and MCP1 respectively (the lower RF the better)

| Structure | A2780 $IC_{50}$ (μM) | A2780/cp70 $IC_{50}$ (μM) | RF1 | MCP1 $IC_{50}$ (μM) | RF2 | Ka ($M^{-1}$) Salmon DNA ($10^4$) | Ka ($M^{-1}$) Calf DNA ($10^4$) |
|---|---|---|---|---|---|---|---|
| AP4-48 | 18.44 ± 1.23 | 16.77 ± 0.54 | 0.9 | 11.7 ± 1.51 | 0.6 | — | — |
| AP4-55 | 2.28 ± 0.23 | 1.59 ± 0.15 | 0.7 | 1.13 ± 0.12 | 0.5 | — | — |

*[1]: No measurable binding via ITC

All of the DIPs show high cytotoxicity apart from the amino acid derivatives LS1-8, LS2-6, and AP8-56, which only show moderate activity. Every cytotoxic DIP also has DNA affinity. The DNA affinity of only one of the three moderately active amino acid derivatives was measured and it is interesting to note that AP8-56 does not have any measurable binding property. The simple addition of a methyl group on AP3-56 to give AP6-96 increases the DNA affinity and the cytotoxicity significantly. Those results suggest a correlation between DNA affinity and cytotoxicity.

The two amino acid stereo-isomers LS2-6 and AP8-56 ((R) and (S) respectively) show moderate cytotoxicity for cisplatin-sensitive cell line A2780, but AP8-56 is significantly more toxic on the two other cisplatin-resistant cell lines A2780/cp70 and MCP1 (RF1=RF2=06). Its (R) stereoisomer counterpart LS2-6 is not as selective and shows moderate cytotoxicity in the three lines.

The simplest of all DIP derivatives, AP5-94, has high cytotoxicity on cisplatin-sensitive A2780 cell line. Its activity on the two other cisplatin-resistant cell lines is interesting: AP5-94 is 50% less active on A2780/cp70 than on A2780, and 50% more active on MCP1 than A2780.

The most cytotoxic molecule is the dodecane derivative LS2-1, which is 790 times more toxic on A2780/cp than the clinical agent carboplatin; 145 times more active on MCP1 than carboplatin and shows a very good cytotoxicity difference between the cisplatin-sensitive cell line and the two resistant cell lines (RF1=RF2=0.6). Increasing the length of the alkyl chain further (LS2-2) decreases the cytotoxicity and reduces the selectivity. The shorter propyl analogue AP10-22 was the least active of all the alkyl DIP derivatives and the intermediate hexyl analogue LS1-95 shows intermediate cytotoxicity. Apart from the longer octadecan derivative LS2-2, all of the alkyl analogues seem to have some sort of selective behaviour on cisplatin-resistant cell lines.

The activity of polymeric DIP derivatives is more difficult to correlate than the monomeric DIPs probably due to difference in solubility and cellular permeability as well as involvement of the spacer. Nevertheless, it can be noted that they tend to be less active than their monomeric counterparts are. Note the high selectivity of AP9-5 dimer (RF1=0.3 and RF2=0.2) and see how the selectivity is reversed just by interchanging the amine with an amide bond (AP8-66) (RF1=1.3). Although the diazinium-bicyclo analogue AP11-36 gains in activity, its selectivity also reverses (RF1=1.5 and RF2=1.3). Therefore, subtle changes on dimeric DIPs 26(t-v) can drastically change their selectivity. Although polymeric DIP tends do be less active than monomeric DIPs, Dimer AP9-5 and trimer AP9-82 offer better selectivity (RF between 0.2 and 0.5).

The DIPys AP4-44 and LS1-16 (respectively the quinolinium and isoquinolinium analogue of DIP AP3-56) show much less cytotoxicity. This could be explained by a decrease in DNA binding affinity. Removing one benzylic moiety is enough to cancel any measurable DNA affinity (see AP4-44). This suggests once more that the cytotoxicity of DIPs is DNA related.

The phenanthridinium secondary amine adducts AP4-20 and AP4-48 show less promising activity and selectivity than the DIPs apart from AP4-55, which shows good cytotoxicity.

Viscosimetry analysis with DIP AP5-94, shows an increase of viscosity similar to the one obtained with the DNA intercalator reference ethidium bromide. Molecule AP5-94 is the simplest DIP framework, and although the rest of the DIPs have not yet been tested, this preliminary result shows DNA intercalating properties of the common aromatic platform.

Medical Uses and Pharmaceutical Compositions

In view of the above results, the compounds of the present invention may be formulated as pharmaceutical and used method of medical treatment, in particular for the treatment of cancer, inflammation, protozoa or to inhibit a topoisomerase.

The properties of the compounds of the invention referred to herein specifically includes both compounds with intrinsic activity (drugs) as well as prodrugs of such compounds, which prodrugs may themselves exhibit little or no intrinsic activity.

The compounds described herein or their derivatives may be formulated in pharmaceutical compositions, and administered to patients in a variety of forms, in particular to treat conditions which are ameliorated by the administration of a compound according to the present invention. Pharmaceutical compositions for oral administration may be in tablet, capsule, powder or liquid form. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parental administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

Suitable carriers, diluents, excipients, etc. can be found in standard pharmaceutical texts such as Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 19th edition, Mack Publishing Company, Easton, Pa., 1995; and Handbook of Pharmaceutical Excipients, 2nd edition, 1994.

In a further aspect, the present invention provides a method of making a pharmaceutical composition comprising admixing at least one compound as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

The pharmaceutically compositions may be given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, Mack Publishing Company, Easton, Pa., 19th edition, 1995.

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 μg to about 250 mg per kilogram body weight of the subject per day, and more typically in dosages of between about 1.0 and 100 mg per kilogram of body weight of the subject per day.

Further, the compositions of the invention may further comprise one or more other pharmaceutically active agents, either further compounds of the invention, or other drugs.

EXPERIMENTAL

Primary Amines

Introduction

In one aspect, the present invention relates to a new class of heterocyclic aromatic cation that is easily prepared in a 'one-pot' reaction system between a phenanthridinium precursor and almost any primary amine with yields that are typically between 61 and 98%, without the need for further purification. Such heterocyclic aromatic cations are currently of great interest due to their high affinity for DNA via intercalation and their application as dyes, probes, and anti-tumour drugs.

The reaction pathway that yields these new heterocyclic aromatic cations has been elucidated and is unprecedented. It was established that the reaction proceeds via three coupled spontaneous reaction steps in a kind of cascade reaction. The sequence of the cascade is: alpha addition, cyclisation followed by an in-situ oxidation step.

The in-situ oxidation step occurs via hydride loss and a second equivalent of the precursor that undergoes the initial alpha addition is also consumed as the hydride acceptor under the reaction conditions. This is the first observation of a reaction system that involves an alpha addition step (removing the aromatic nature of the ring) followed by cyclisation and spontaneous re-aromatisation of the ring via hydride loss.

The intermediates of the cascade reaction have been characterised in solution using a novel NMR-phase transfer procedure. This provides strong support for the assignment of the proposed reaction pathway.

A route to the systematic variation of desired properties is given by the ability to form the target molecules with almost any type of primary amine; furthermore, the same process can occur with the quinolinium derivative. The wider applicability of this reaction means that it will find great utility in organic synthesis.

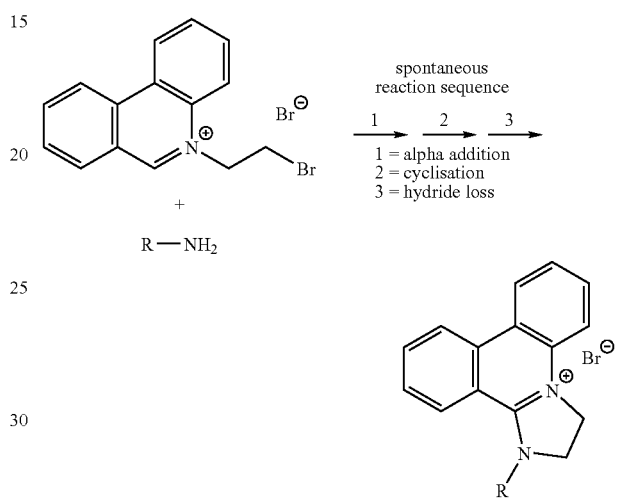

The present invention relates to a new class of heterocyclic aromatic cation which has been isolated from the reaction of a 2-bromo-ethyl-phenanthridinium bromide with several types of primary amine in excellent yields. The reaction pathway has been found to proceed via an alpha addition step followed by cyclisation to form a five-membered ring as an imidazolidine-based intermediate. The imidazolidine intermediate then undergoes hydride loss, yielding a rearomatized dihydro-1H-imidazo[1,2-f]phenanthridinium moiety; this process occurs by hydride transfer to a second equivalent 2-bromo-ethyl-phenanthridinium bromide. Furthermore, this cascade reaction appears to be general for all types of primary amine and has also been extended by replacing the phenanthridinium moiety by a quinolinium derivative.

Surprisingly, despite their wide application, previous work exploring ring extensions of the phenanthridinium core has been limited to the aromatic cycles a and c leaving the heteroaromatic middle ring b, unexplored.

Herein, an unprecedented reaction system is presented that allows the isolation of a new class of heteroaromatic framework through a ring-extension process. This ring extension involves the central ring b of the phenanthridinium core in the formation of a five-membered ring, comprising a dihydro-imidazo moiety. This moiety is derived from the phenanthridinium core whereby primary amine 1 reacts (in DMF) with 2-bromo-ethyl-phenanthridinium bromide 2 to give 2,3-dihydro-1H-imidazo[1,2-f]phenanthridinium, molecule 6 (Scheme 1). The formation of 6 can be explained by two distinctive pathways; pathway A involves the following processes: alpha addition, cyclisation and in situ oxidation reaction, via a hydride loss, whereas pathway B involves nucleophilic substitution at the ethyl-bromide side chain before cyclisation and hydride loss.

Scheme 1. The two hypothetical reaction pathways, along with intermediates, to the new heteroaromatic cation framework 6(a-j).
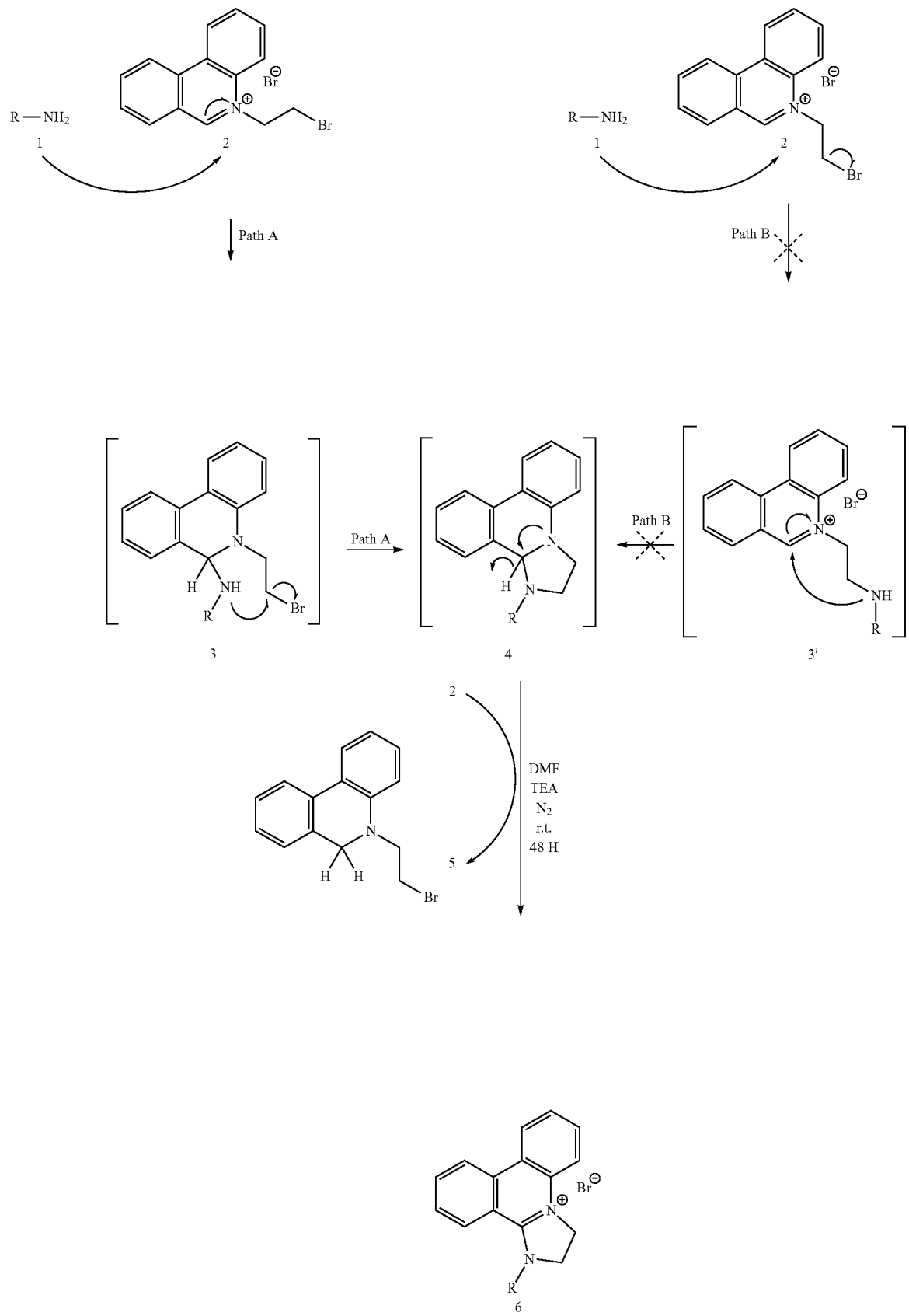

The nature of this reaction seems not to depend on the amine employed because, by using one general synthetic procedure, a large variety of amines were found to undergo the same transformation in excellent yields, including aromatic amines (Table 1). The synthetic procedure itself is extremely simple (see experimental section) and the products 6(a-k) isolated by precipitation are found to be analytically pure (see supplementary details for full analytical data).

TABLE 1

Results from preliminary studies showing that the reaction is general for all types of primary amine.

| Entry | Structure | Primary amine 1 | Yield (%) |
|---|---|---|---|
| 6a | 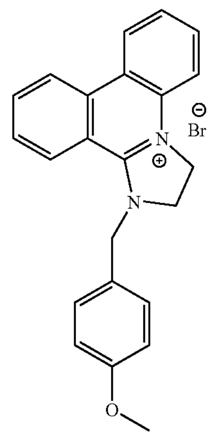 | 4-Methoxybenzylamine | 95 |
| 6b | 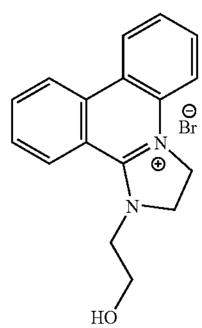 | Ethanolamine | 98 |
| 6c | 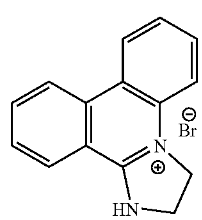 | Ammonia | 61 |
| 6d | 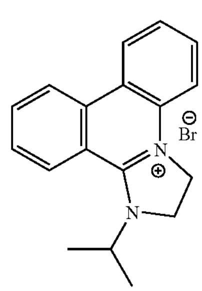 | Isopropylamine | 82 |

TABLE 1-continued

Results from preliminary studies showing that the reaction is general for all types of primary amine.

| Entry | Structure | Primary amine 1 | Yield (%) |
|---|---|---|---|
| 6e | 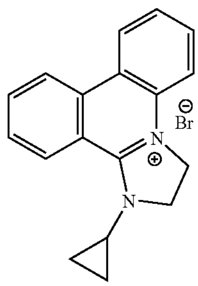 | Cyclopropylamine | 78 |
| 6f | 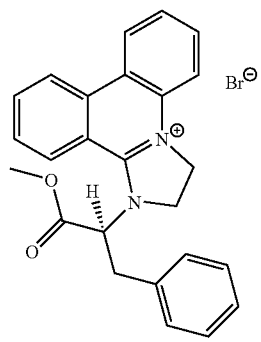 | L-alanine methoxycarbonyl | 63 |
| 6g | 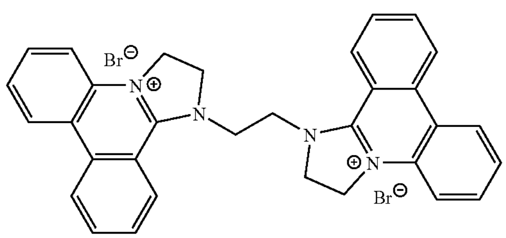 | Ethylene diamine | 98 |
| 6h | 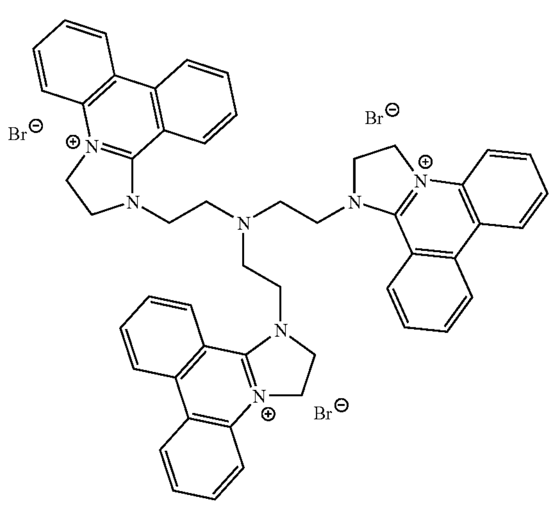 | tris(2-Aminoethyl)amine | 95 |

TABLE 1-continued

Results from preliminary studies showing that the reaction is general for all types of primary amine.

| Entry | Structure | Primary amine 1 | Yield (%) |
|---|---|---|---|
| 6i | 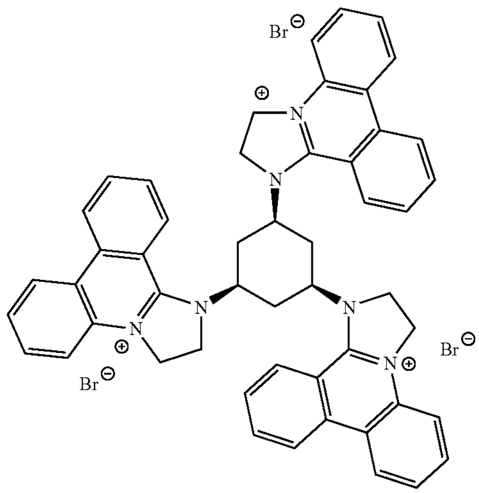 | cis(1,3,5-Triaminocyclohexane) | 91 |
| 6j | 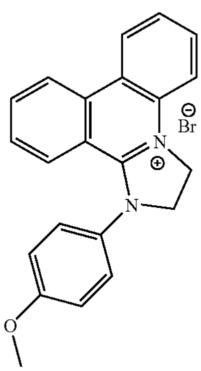 | 4-Methoxyaniline | 74 |
| 6k | 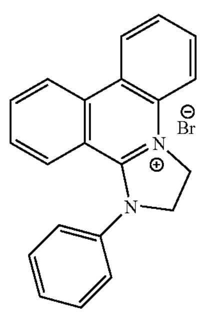 | Aniline | 73 |

Strong evidence in favor of pathway A has been found. Firstly, intermediate 4d was isolated via a phase transfer reaction in an NMR tube whereby the reaction is initiated in a biphasic solvent system containing $D_2O$ and $CDCl_3$ (1:1). In this way, the first step of the reaction takes place in the $D_2O$ layer, but the second step proceeds in the organic layer as 3, insoluble in $D_2O$, immediately shifts toward the chlorinated phase once it is formed. Cyclisation occurs spontaneously, yielding molecule 4, which is soluble in organic solvents and therefore, reaction with molecule 2 is prevented. The redox step, which involves hydride transfer from molecule 4 to molecule 2, cannot occur and this allows 4d to be unambiguously identified (see supplementary data for details).

However, the postulated second intermediate 4 is common to both pathways (Scheme 1), and isolation of intermediate 3 and/or 3' is required to aid mechanistic analysis. To investigate this, experiments were devised and conducted to examine the intermolecular reactivity between the amine and the aromatic alpha position of the fluoro- and hydroxy-analogues of molecule 2, (7a and 7b, respectively. Scheme 2). In conducting these experiments, we assumed that the electrophilic nature and hence reactivity of the alpha position in analogues 7a and 7b is similar to that of molecule 2. However, these analogues are unable to cyclise and therefore the reaction does not proceed past the alpha addition step, but provide us with circumstantial evidence regarding the reactivity of the alpha position in molecule 2.

Scheme 2. NMR phase transfer experiment with the fluoro (7a) and hydroxy (7b) analogues of molecule 2.

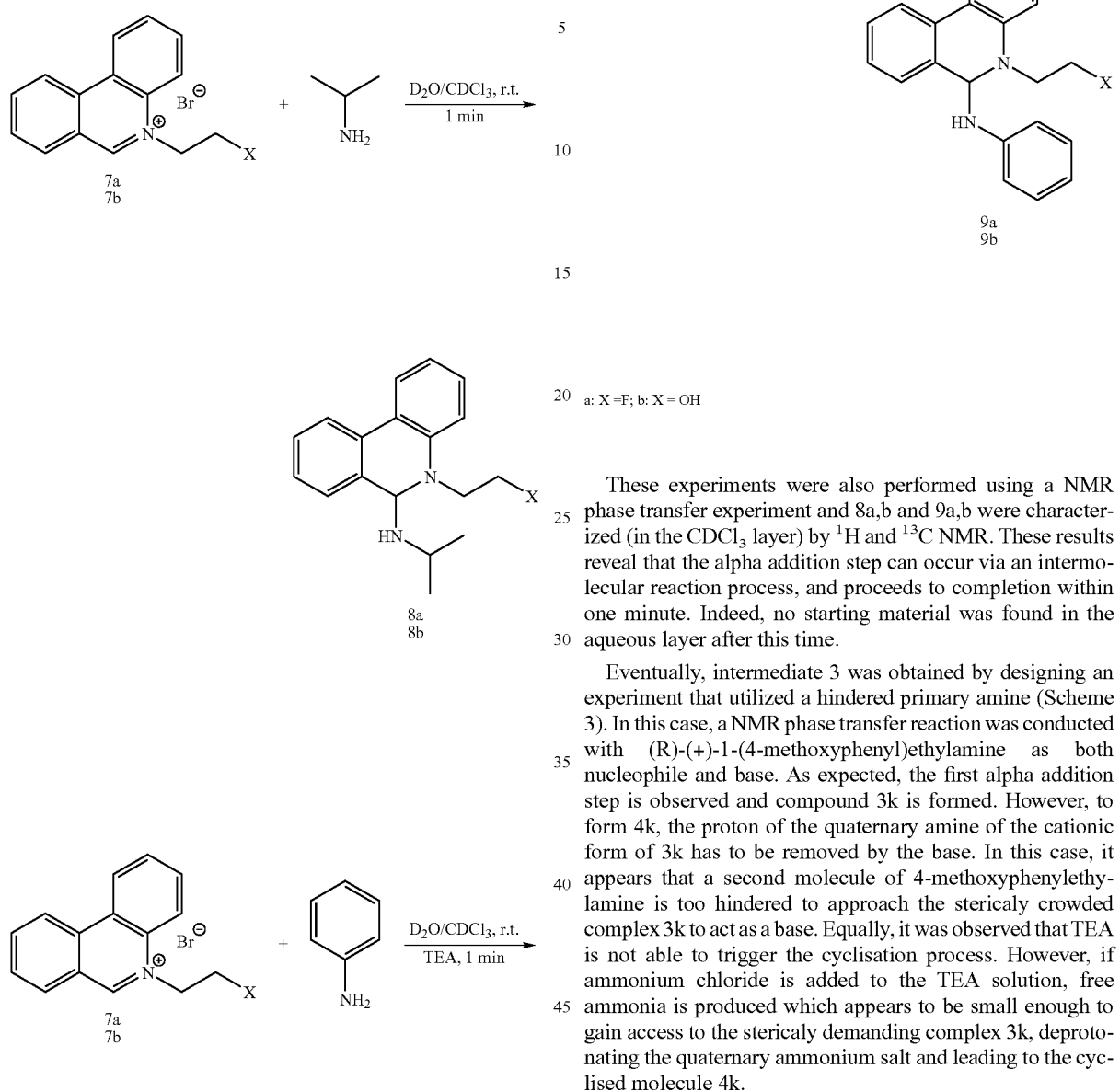

a: X = F; b: X = OH

These experiments were also performed using a NMR phase transfer experiment and 8a,b and 9a,b were characterized (in the CDCl$_3$ layer) by $^1$H and $^{13}$C NMR. These results reveal that the alpha addition step can occur via an intermolecular reaction process, and proceeds to completion within one minute. Indeed, no starting material was found in the aqueous layer after this time.

Eventually, intermediate 3 was obtained by designing an experiment that utilized a hindered primary amine (Scheme 3). In this case, a NMR phase transfer reaction was conducted with (R)-(+)-1-(4-methoxyphenyl)ethylamine as both nucleophile and base. As expected, the first alpha addition step is observed and compound 3k is formed. However, to form 4k, the proton of the quaternary amine of the cationic form of 3k has to be removed by the base. In this case, it appears that a second molecule of 4-methoxyphenylethylamine is too hindered to approach the stericaly crowded complex 3k to act as a base. Equally, it was observed that TEA is not able to trigger the cyclisation process. However, if ammonium chloride is added to the TEA solution, free ammonia is produced which appears to be small enough to gain access to the stericaly demanding complex 3k, deprotonating the quaternary ammonium salt and leading to the cyclised molecule 4k.

Scheme 3. Isolation of intermediate 3k.

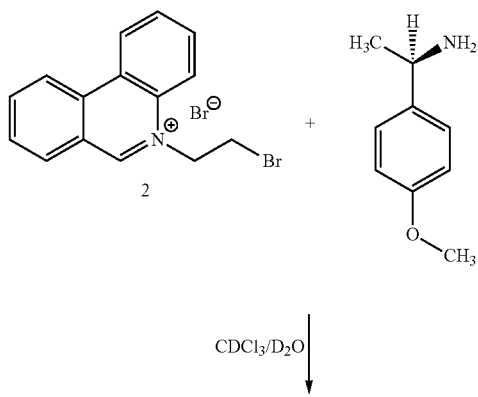

CDCl$_3$/D$_2$O ↓

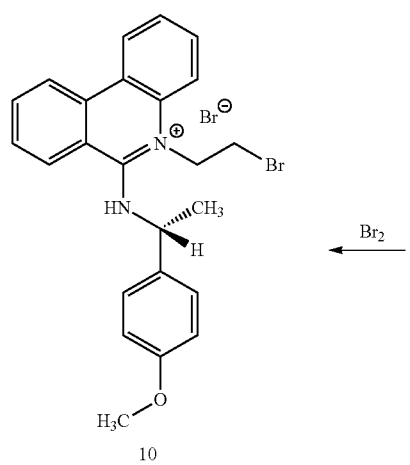

10

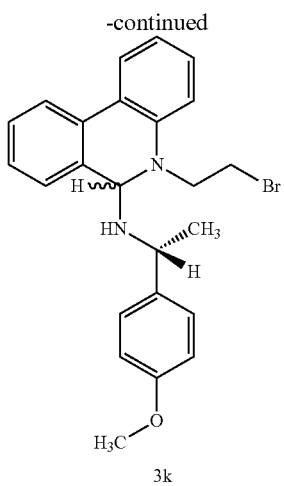

3k

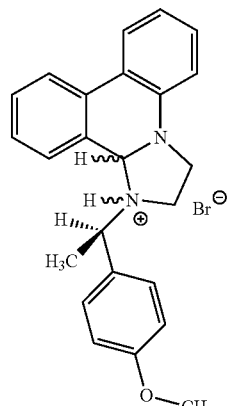

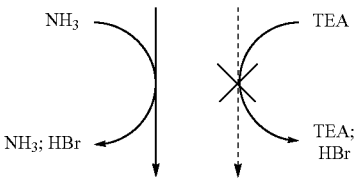

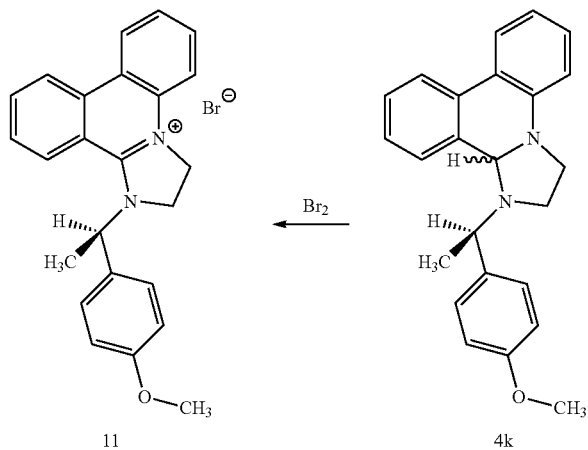

11  4k

Interestingly, ammonia does not react at the ethyl-bromide side chain via a nucleophilic substitution. This is explained by the fact that the deprotonation of a quaternary amine is many orders of magnitude faster. This kinetic argument can also be applied to the intramolecular five membered ring cyclisation, which occurs much faster compared to the intermolecular reaction pathway. Note that 3k and 4k can be oxidized by bromine to 10 and 11, respectively. Therefore, our experimental data allows us to propose pathway A (alpha addition, cyclisation and hydride loss) as being the mechanistic pathway taken in the synthesis of the molecules of the type 6, shown in Scheme 1.

Pathway A is initiated by reaction of the amine with 2 via an addition at the sp$^2$ hybridized carbon in α position to the quaternary ammonium centre. The newly formed secondary amine 3 is then subject to a favoured 5-exo-tet cyclisation[17] yielding the intermediate imidazolidine 4. Intermediate 4 is in turn subject to an oxidative process via the loss of a hydride in the presence of another equivalent of 2, which is consumed as an oxidizing agent. The isolation and characterization of the by-product 5 provides strong agreement for the last in-situ oxidation step. Interestingly, this process does not interfere with the purification of 6 as by-product 5 remains in solution during precipitation of the final product. Furthermore, because of the high yield obtained with each of the primary amines tested, the in-situ oxidation step appears to be irreversible under the reaction conditions studied. It could be suggested that the positive charge on the quaternary ammonium ion in 6 is stabilized by the mesomeric donor effect of the nitrogen from the secondary amine. This idea is supported by the X-ray crystallographic structural analysis of [C₂₃H₂₁N₂O]Br.CHCl₃, 6a, which clearly shows the conjugation between the two nitrogen atoms.

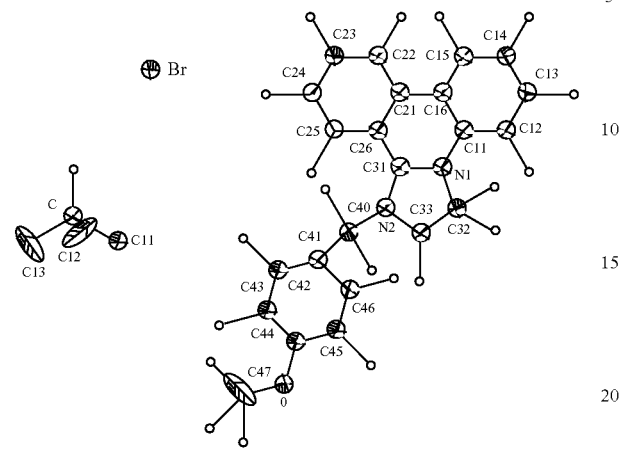

ORTEP representation of the structure of compound 6a.
Selected bond lengths [Å]: N2-C31 1.333(3), N2-C33 1.472(3), N2-C40 1.457(3), N1-C31 1.340(3), N1-C11 1.389(3), N1-C32 1.475(3).

The shortening of the carbon-nitrogen bond N2-C31 compared to N2-C33 and N2-C40 indicates that it has partial double bond character and the similar bond lengths for N2-C31 and C31-N1 indicates that the bonding electron density is evenly shared between these three atoms. Also, it may be hypothesized that the dihydro-imidazole component of 6 has less steric strain than the imidazolidine part of 4. Therefore, the formation of the double bond during hydride loss releases steric strain in the ring. Thus, the reduction in steric strain may enhance the effectiveness of the oxidation step. Finally, during the oxidation process of 4 to 6, the central cycle regains its aromatic character and so restores conjugation between the aromatic cycles a and c. To summarize, three factors appear to contribute to the effectiveness of the hydride transfer: (i) mesomeric stabilization of the quaternary ammonium salt, (ii) relaxation of the five membered heterocyclic ring upon formation of a double bond and (iii) the rearomatisation of heterocycle b enhancing the conjugation of the system.

To examine the application of the reaction to other aromatic systems, the synthesis of an already existing framework, in this case 2,3-dihydro-1H-imidazo[1,2-a]quinolinium bromide derivative was investigated from 2-bromo-ethyl-quinolinium bromide, 12, as a precursor (Scheme 4). By employing an identical procedure, product 13 was isolated in a 70% yield. The success of this reaction demonstrates that the quinolinium framework is also amenable to this type of methodology.

Scheme 4. Cascade reaction with the quinolinium derivative.

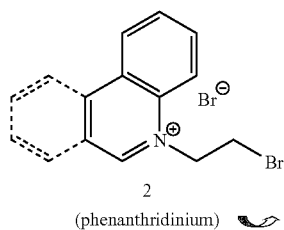

2
(phenanthridinium)

-continued

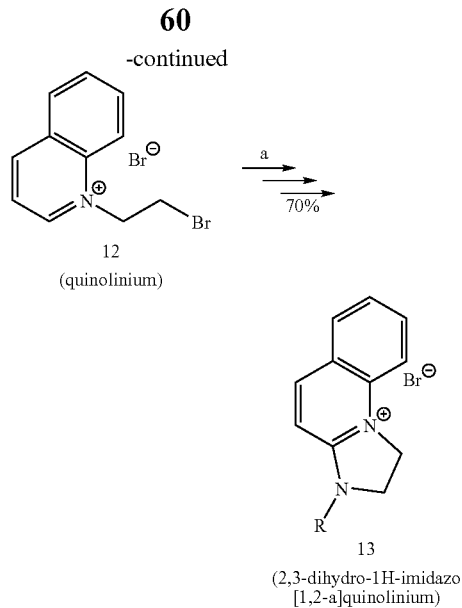

a: 4-methoxybenzylamine, DMF, TEA, N₂, r.t., 48 h
R = methoxybenzyl

In conclusion, we have developed an innovative type of reaction that yields heteroaromatic cations and appears to be general and effective. It is remarkable that the simple reaction system described here allows facile formation of a new subset of phenanthridinium heterocycle. Such molecules are interesting to develop new types of DNA intercalating framework and the cascade reaction will find utility in organic synthesis. Notably, the observation and elucidation of the spontaneous reaction sequence—alpha addition, cyclisation and hydride loss—is unprecedented.

Secondary Amines

The non-SN₁ non-SN₂ mechanism of 2-bromo-ethyl-phenanthridinium with secondary amine.

Reaction of 2-bromo-ethyl-phenanthridinium (2) with secondary amines in our redox condition leads to the substitution product (14):

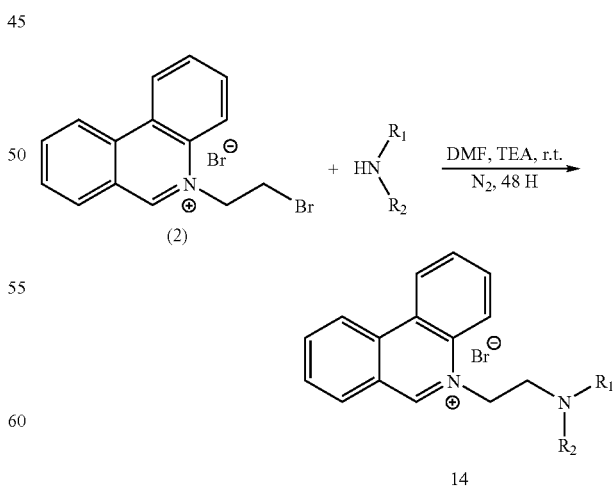

At first sight, it looks like a usual SN₂ mechanism but we have demonstrated that it is not. Two mechanisms can explain the formation of the secondary substitution product (14):

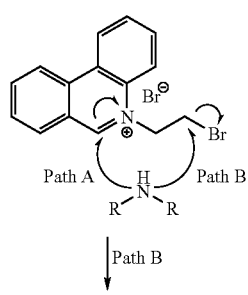

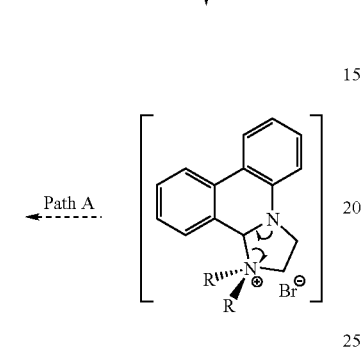

With the help of the phase transfer reaction, we have seen that any nucleophile reacts on 2-bromo-ethyl-phenanthridinium (2) via a first steep alpha addition. Therefore, the first intermediate could be:

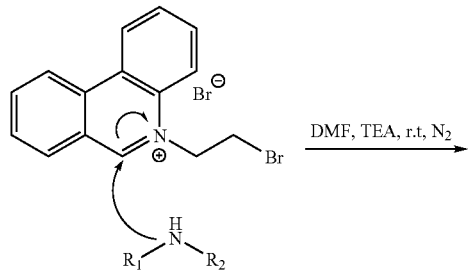

The following piperidine alpha-adduct and (4-Methoxyphenyl)-methanethiol alpha-adduct were isolated in CDCl$_3$ solution of an NMR tube:

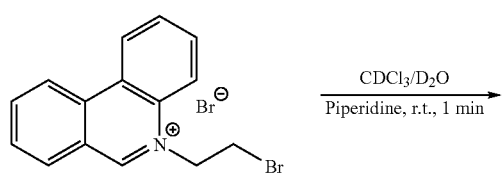

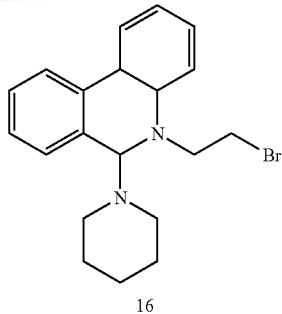

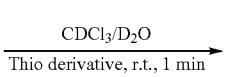

Like with primary amine, in a polar solvent like DMF, this first intermediate should undertake a rapid 5-exo-tet-cyclisation to yield a second intermediate:

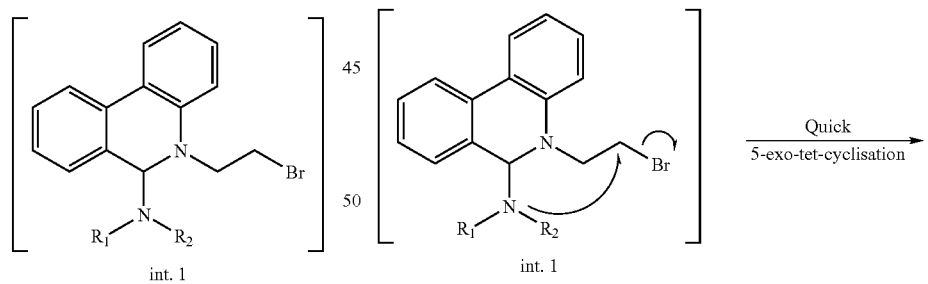

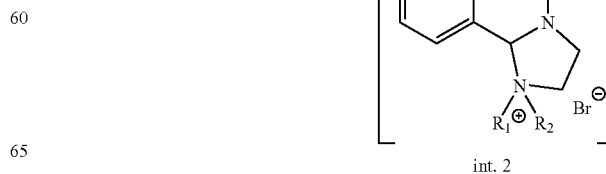

Next, a 5-membered ring oxidative re-opening should happen:

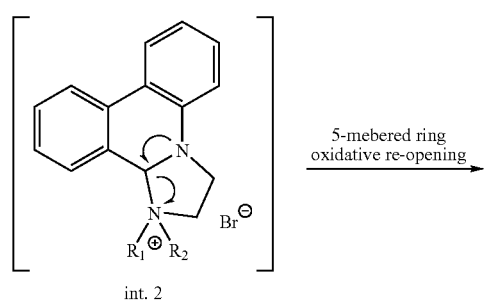

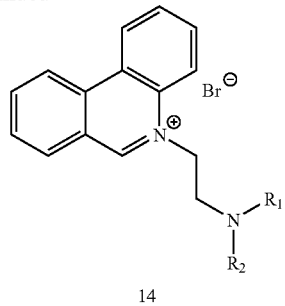

To test this last hypothesis we have protonated one intermediate of the primary amine reaction:

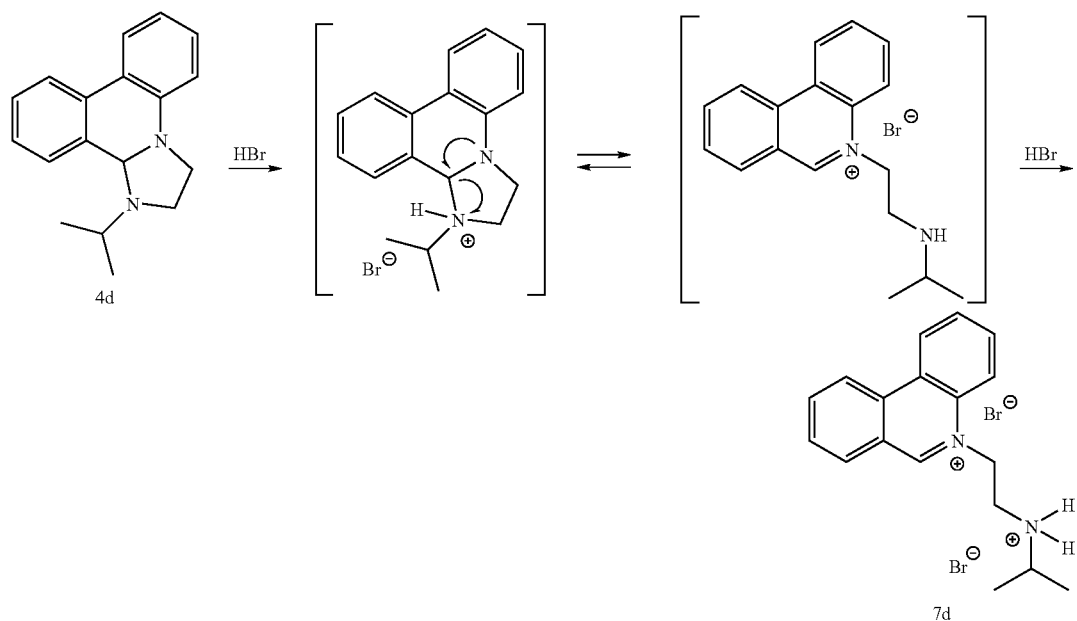

Upon protonation, a ring opening occurs leading to re-aromatisation. The re-aromatisation being the driving force. Therefore, we are confident in stating that the mechanism of the reaction with secondary amine is not a usual $SN_2$ mechanism, but rather a "non-$SN_1$ non-$SN_2$ substitution involving an intramolecular rearrangement:

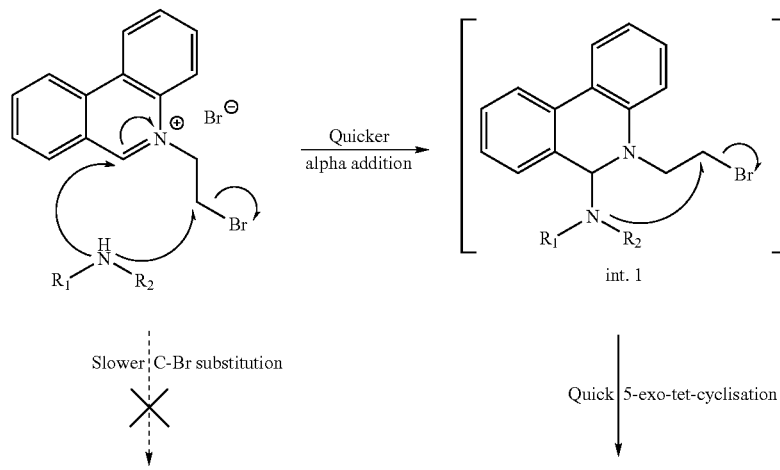

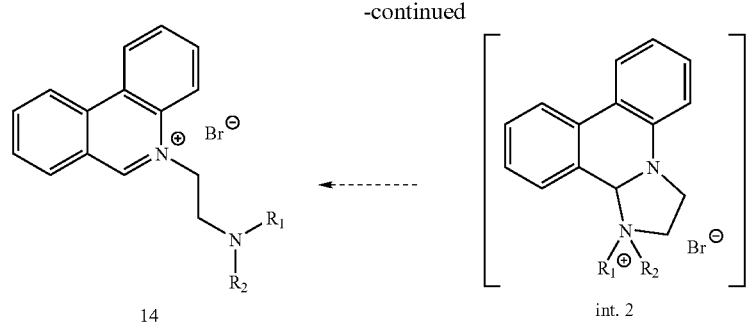
Thio-compound should follow the same mechanism:
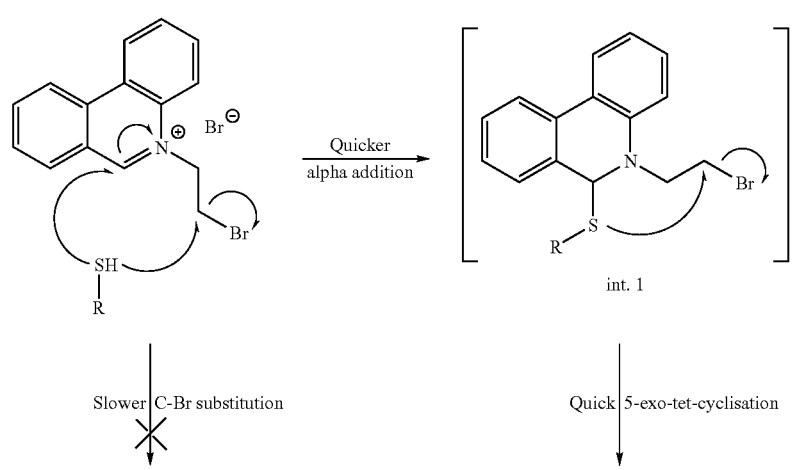
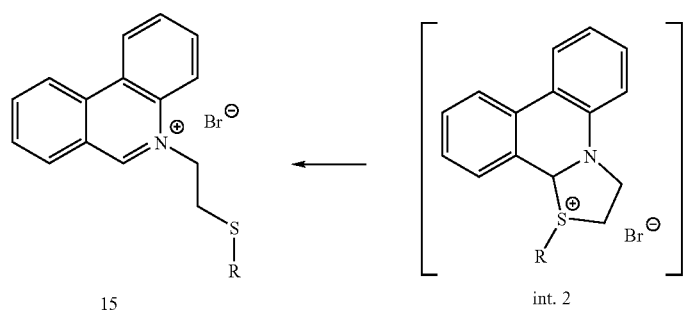

Molecules obtained via the non SN₁ non SN₂ mechanism:
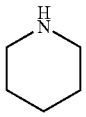
| Nucleophile | Product | Yield (%) |
|---|---|---|
| 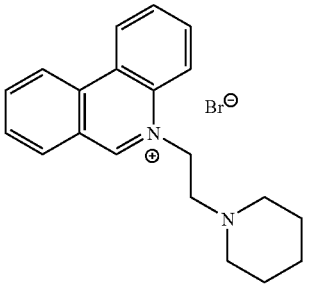 Piperidine | 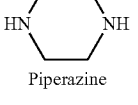 14a | 71 |
| 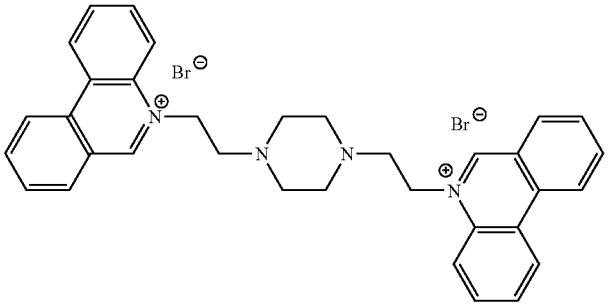 Piperazine | 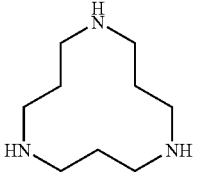 14b | 73 |
| 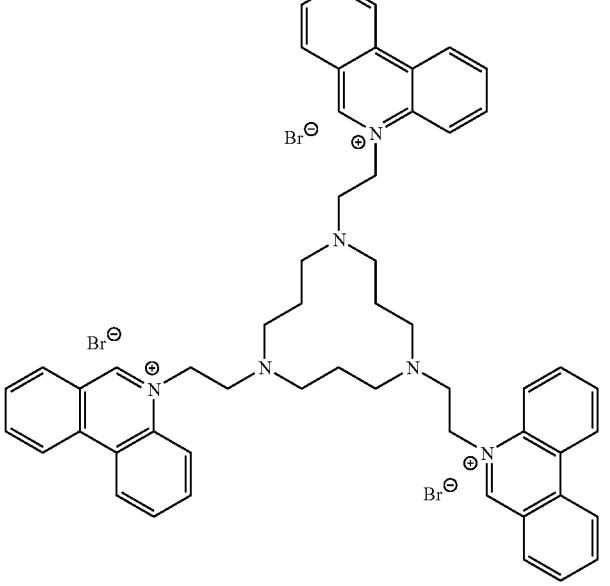 1,5,9 triaza-Cyclododecane | 14c | 93 |

| Nucleophile | Product | Yield (%) |
|---|---|---|
| 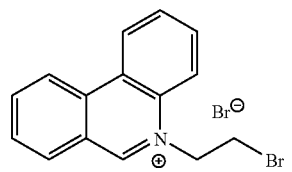 Paramethoxybenzyl Mercaptan | 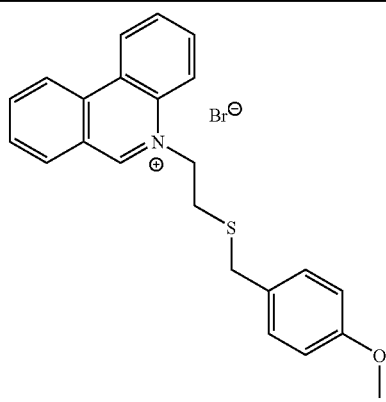 15 | 76 |

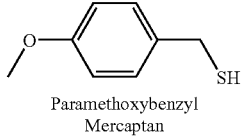

A notable advantage of this non-SN$_1$ non-SN$_2$ mechanism over a conventional substitution reaction lay in the more reactivity of the first conditions. A usual substitution on the 2-bromo-ethyl side chain would require more energetic conditions. Even aromatic primary amines do the first alpha addition at r.t. Likewise, secondary amines start the first alpha addition step in mild condition and lead, after rearrangement, to the final substituted product.

Instrumentation and Materials

All reactions were carried out using oven-dried glassware under a nitrogen atmosphere using standard Schlenk techniques. Commercial starting materials and solvents were used as supplied, without further purification.

$^1$H NMR and $^{13}$C NMR were recorded using a Bruker DPX 400 spectrometer operating at 400 and 100 MHz, respectively. Chemical shifts (δ) are given in ppm relative to residual solvent peak. Coupling constants (J) are given in Hz. The multiplicities are expressed as follows: s=singlet, d=doublet, t=triplet, q=quartet. Infra-red spectral analysis were performed on a JASCO 410 spectrophotometer, using a KBr disc unless otherwise stated; peaks are quoted in wave numbers (cm$^{-1}$) and their relative intensity are reported as follows: s=strong, m=medium, w=weak. Mass spectra were obtained using a JEOL JMS 700 spectrometer operating, in FAB, EI, CI or ES mode. Microanalyses were performed on a CE-440 elemental analyzer. Melting points were determined on a digital IA9000 series melting point apparatus, using capillary tubes.

Definitions of Abbreviations

DMF=Dimethylformamide; TEA=Triethylamine; DCM=Dichloromethane; r.t.=Room temperature.

Preparation and Physical Data of the Molecules

Formula A Compounds

1. Preparation of 2-Bromo-ethyl-phenanthridinium bromide (2)

Phenanthridine (5.44 g; 30.4 mmol) was dissolved in 1,2-Dibromoethane (114.2 g; 52 ml; 608 mmol) and stirred at 110° C. for three days. During that time, a white precipitate was formed and was filtered off every 12 hours. After each filtration, the precipitate was rinsed with an additional 5 ml of 1,2-Dibromoethane and the mother liquor was stirred at 90° C. until the next filtration. The reaction was complete after ca. three days when no more precipitate formed. The filtrates were combined and washed thoroughly with ether and with ethyl acetate to give 2 (7.92 g; 21.6 mmol) as a beige powder in a 95% yield; mp: 234-235° C. (dec.); $^1$H NMR (D$_2$O, 400 MHz): δ 9.81 (s, 1H), 8.72 (d, 1H, J=7.2 Hz), 8.63 (d, 1H, J=7.2 Hz), 8.37 (d, 1H, J=7.2 Hz), 8.26 (d, 1H, J=7.2 Hz), 8.18 (t, 1H, J=7.2 Hz), 7.98 (t, 1H, J=7.2 Hz), 7.90 (m, 2H), 5.37 (t, 2H, J=5.8 Hz), 4.05 (t, 2H, J=5.8 Hz); $^{13}$C NMR (D$_2$O, 100 MHz): δ 155.27 (CH), 139.03 (CH), 135.59 (C), 133.18 (CH), 132.78 (C), 132.58 (CH), 130.85 (CH), 130.72 (CH), 126.57 (C), 125.13 (CH), 123.32 (C), 123.00 (CH), 118.91 (CH), 58.87 (CH$_2$), 29.41 (CH$_2$); IR (KBr, cm−1): 2947(w), 1620(m), 763(s), 717(m); MS (ES): 288.1 (M−Br) (100), 206.2 (8); Anal. Calcd for C$_{15}$H$_{13}$NBr$_2$: C, 49.32; H, 3.59; N, 3.84. Found: C, 49.15; H, 3.48; N, 3.76.

2. Isolation and Characterisation of 5-(2-Bromo-ethyl)-5, 6-dihydro-phenanthridine (5)

During the preparation of 6a, the mother liquor from the DMF/ether (25:75) solution was kept and washed thoroughly 4 times with 40 ml of water. The organic layer was then washed with brine and dried over MgSO$_4$. The solvent was evaporated down to a dark residue. Column chromatography (Silica, DCM as elutant) afforded 5 (140 mg; 0.485 mmol) as a beige powder in a 50% yield. R$_f$=0.75 in 100% ethyl acetate; mp: 99-100° C.; 1H NMR (CDCl$_3$, 400 MHz): δ 7.64 (d, 1H, J=7.60 Hz), 7.60 (d, 1H, J=7.60 Hz), 7.22 (t, 1H, J=7.60 Hz), 7.13 (t, 2H, J=7.60 Hz), 7.01 (d, 1H, J=7.60 Hz), 6.77 (t, 1H, J=7.60 Hz), 6.62 (d, 1H, J=7.60 Hz), 4.27 (s, 2H), 3.64 (t, 2H, J=7.80 Hz), 3.44 (t, 2H, J=7.80 Hz); 13C NMR (CDCl3, 100 MHz): δ 145.02 (C), 132.71 (C), 132.19 (C), 129.68 (CH), 128.55 (CH), 128.22 (CH), 125.96 (CH), 124.44 (CH), 124.22 (C), 123.59 (CH), 119.19 (CH), 112.51 (CH), 53.38 (CH$_2$), 53.26 (CH$_2$), 27.78 (CH$_2$); IR (KBr, cm−1): 3429 (s), 2924 (w), 1716 (w), 1628 (s), 1601 (s), 1525 (w), 1493 (s), 1442 (s), 1340 (m), 1290 (s), 1269 (s), 1196 (s), 1022 (m), 758 (s), 725 (m), 615 (m) MS (FAB): 289 (M+H) (100), 222.1 (7), 194.1 (35), 180.1 (22), 166.1 (6), 152.1 (4), 107.2 (2), 85.7 (1), 58.1 (7); Anal. Calcd for C$_{15}$H$_{14}$NBr: C, 62.51; H, 4.89; N, 4.86. Found: C, 62.30; H, 4.96; N, 4.75.

3. Preparation and Characterisation of 1-Isopropyl-1, 2,3,12b-tetrahydro-imidazo[1,2-f]phenanthridine (4d)

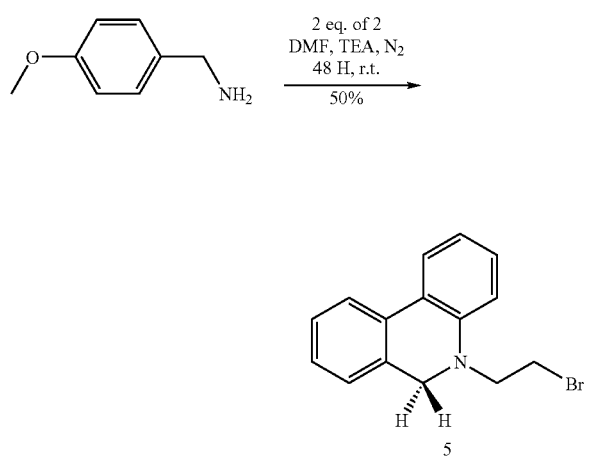

In an NMR tube, compound 2 (10 mg; 0.027 mmol) was dissolved in D$_2$O (0.6 ml). CDCl$_3$ (0.6 ml) was added followed by isopropylamine (2.3 μl; 1.60 mg; 0.027 mmol) used as a reactant and as a base. The NMR tube was shaken energetically for 1 minute to allow the phase transfer process to occur. 1H and 13C NMR spectra were taken of the CDCl$_3$ layer and the organic layer was then isolated for MS and IR analysis; this in situ NMR experiment was required as attempts to scale up the reaction were unsuccessful due to the highly unstable nature of the molecule 4d to oxidation. 1H NMR (CDCl$_3$, 400 MHz): δ 7.77 (d, 1H, J=7.8 Hz), 7.74 (d, 1H, T=7.2 Hz), 7.47 (d, 1H, J=6.4 Hz), 7.35 (m, 2H), 7.25 (d, 1H, J=7.6 Hz), 6.92 (t, 1H, J=7.6 Hz), 6.73 (d, 1H, J=7.8 Hz), 4.73 (s, 1H), 3.47 (m, 1H), 3.25 (m, 4H), 1.25 (d, 3H, J=6.4 Hz), 1.12 (d, 3H, J=6.4 Hz); 13C NMR (CDCl$_3$, 100 MHz): δ 144.34 (C), 135.76 (C), 132.00 (C), 129.34 (CH), 127.88 (CH), 127.66 (CH), 124.13 (CH), 123.85 (CH), 123.39 (C), 123.32 (CH), 119.07 (CH), 113.45 (CH), 76.72 (CH), 51.68 (CH), 46.86 (CH$_2$), 45.07 (CH$_2$) 22.63 (CH$_3$), 17.21 (CH$_3$); Solution IR with KBr windows (cm−1): 3680 (m), 3022 (s), 2968 (w), 2436 (w), 2398 (s), 1602 (w), 1522 (m), 1480 (m), 1426 (m), 1387 (w), 1136 (w), 1219 (s); MS (CI): 265.2 (M+1) (20), 195.1 (5), 180.1 (12), 127.1 (10), 119.1 (32), 102.2 (22), 89.1 (100).

4. General Procedure for the Preparation of 2,3-Dihydro-1H-imidazo[1,2-f]phenanthridinium bromide derivatives (6a-k)

2-Bromo-ethyl-phenanthridinium bromide (2) (700 mg; 1.9 mmol) was suspended in DMF (20 ml). Primary amine (0.95 mmol) and TEA (795 μl; 5.7 mmol) were added successively to the stirred solution. After stirring for 48 hours at r.t. under nitrogen the final product and TEA hydrobromide salt were precipitated from the solution with diethyl ether (100 ml), and this was recovered by filtration. The precipitate washed thoroughly with diethyl ether and ethyl acetate and then triturated with 1 ml of water to remove the TEA salt, yielding the 2,3-Dihydro-1H-imidazo[1,2-f]phenanthridinium bromide derivative (6a-j). In some rare cases the product was purified further by recrystallisation from methanol/ethyl acetate (50:50).

a. 1-(4-Methoxy-benzyl)-2,3-dihydro-1H-imidazo[1,2-f]phenanthridin-4-ylium bromide (6a):

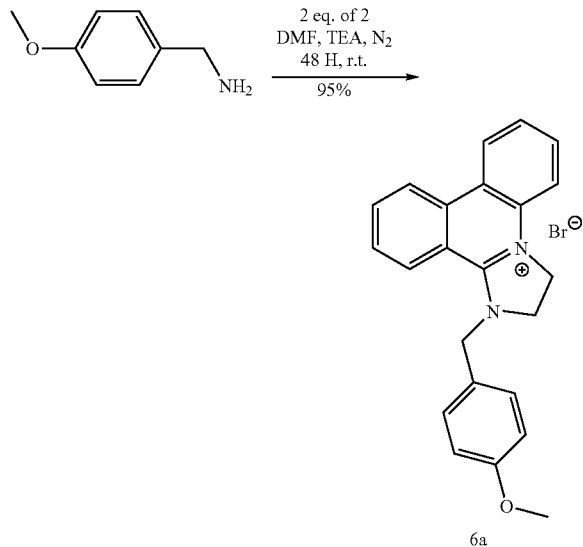

6a (380 mg; 0.9 mmol) was obtained as an off white powder in a 95% yield; mp: 245-246° C. (dec.); $^1$H NMR (CDCl$_3$, 400 MHz): δ 8.52 (d, 1H, J=8.2 Hz), 8.36 (d, 1H, J=8.2 Hz), 8.21 (d, 1H, J=8.2 Hz), 7.93 (t, 1H, J=8.2 Hz), 7.69 (t, 1H, J=8.2 Hz), 7.56 (t, 1H, J=8.2 Hz), 7.51 (m, 2H), 7.32 (d, 2H, J=8.2 Hz), 6.91 (d, 2H, J=8.2 Hz), 5.41 (s, 2H), 5.04 (t, 2H, J=10.6 Hz), 4.68 (t, 2H, J=10.6 Hz), 3.76 (s, 3H); $^{13}$C NMR (CDCl$_3$, 100 MHz): δ 160.26 (C), 154.91 (C), 136.30 (C), 135.79 (CH), 133.25 (C), 132.25 (CH), 129.49 (CH), 128.34 (CH), 127.94 (CH), 126.28 (CH), 125.29 (C), 124.42 (CH), 123.96 (CH), 120.93 (C), 116.38 (CH), 115.91 (C), 115.40 (CH), 55.81 (CH$_3$), 55.36 (CH$_2$), 52.54 (CH$_2$), 47.72 (CH$_2$) IR (KBr, cm$^{-1}$): 3431(s), 2924(w), 2360(w), 1612(s), 1576 (s), 1514(m), 1456(m), 1304(m), 1248(m) 1026(m), 814(m), 754(m); MS (FAB): 341.2 (M−Br) (35), 232 (10), 157.1 (56), 121.2 (13), 79.7 (100); Anal. Calcd for C$_{23}$H$_{21}$N$_2$OBr. 0.5H$_2$O: C, 64.19; H, 5.15; N, 6.51. Found: C, 64.87; H, 5.47; N, 6.95.

b. 1-(2-Hydroxy-ethyl)-2,3-dihydro-1H-imidazo[1,2-f]phenanthridin-4-ylium bromide (6b)

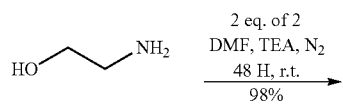

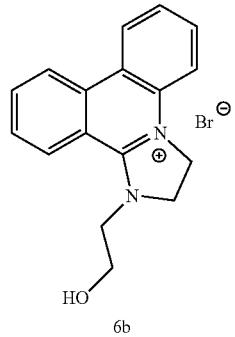

6b (320 mg; 0.93 mmol) was obtained as a pale yellow crystalline solid in a 98% yield; mp: 270-271° C. (dec.); $^1$H NMR (D$_2$O, 400 MHz): δ 8.23 (d, 2H, J=8.2 Hz), 8.11 (d, 1H, J=8.2 Hz), 7.86 (t, 1H, J=8.2 Hz), 7.64 (t, 2H, J=8.2 Hz), 7.43 (t, 1H, J=8.2 Hz), 7.20 (d, 1H, J=8.2 Hz), 4.35 (t, 2H, J=11 Hz), 4.22 (t, 2H, J=11 Hz), 4.09 (t, 2H, J=5.2 Hz), 4.03 (t, 2H, J=5.2 Hz); $^{13}$C NMR (D$_2$O, 100 MHz): δ 153.47 (C), 135.59 (CH), 134.59 (C), 132.13 (C), 131.63 (CH), 129.30 (CH), 127.68 (CH), 125.67 (CH), 123.63 (CH), 123.29 (CH), 119.59 (C), 115.42 (CH), 114.73 (C), 59.10 (CH$_2$), 52.54 (CH$_2$), 51.45 (CH$_2$), 45.80 (CH$_2$); IR (KBr, cm$^{-1}$): 3433 (s), 2922 (w), 2360 (w), 1603 (s), 1576 (s), 1520 (w), 1456 (m), 1387 (w), 1302 (m), 1265 (m), 1084 (m), 874 (w), 758 (m); MS (FAB): 265.2 (M−Br) (100), 219.1 (12), 178.1 (5), 154.1 (2), 136.1 (2); Anal. Calcd for C$_{17}$H$_{17}$N$_2$OBr: C, 59.14; H, 4.96; N, 8.11; Found: C, 58.67; H, 4.78; N, 7.92.

c. 2,3-Dihydro-1H-imidazo[1,2-f]phenanthridin-4-ylium bromide (6c)

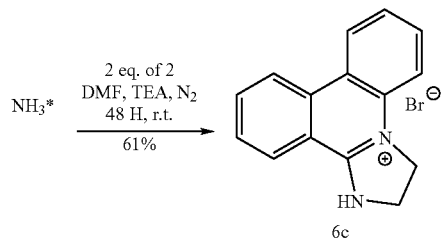

6c (250 mg; 0.83 mmol) was obtained as a yellow powder in a 61% yield; mp: 392-394° C. (dec.); $^1$H NMR (D$_2$O, 400 MHz): δ 7.83 (d, 1H, T=8.0 Hz), 7.79 (d, 1H, J=8.0 Hz), 7.66 (t, 1H, J=8.0 Hz), 7.46 (m, 3H), 7.28 (t, 1H, J=8.0 Hz), 6.93 (d, 1H, J=8.0 Hz), 4.13 (t, 2H, J=10.8 Hz), 3.91 (t, 2H, J=10.8 Hz); $^{13}$C NMR (D$_2$O, 100 MHz): δ 154.69 (C), 135.75 (CH), 133.18 (C), 131.65 (C), 129.56 (CH), 126.26 (CH), 125.65 (CH), 123.40 (CH), 123.01 (CH), 119.25 (C), 115.45 (CH), 113.64 (C), 47.62 (CH$_2$), 43.04 (CH$_2$); IR (KBr, cm$^{-1}$): 3435 (s), 3028 (m), 2997 (m), 2950 (m), 2773 (w), 2684 (w), 2050 (w), 1626 (s), 1608 (s), 1585 (s), 1469 (m), 1454 (m), 1358 (m), 1294 (m), 1267 (w), 1169 (w), 1022 (w), 754 (s); MS (EI+): 220 (M−Br) (10), 219.3 (12), 142.3 (8), 112.2 (5), 100.2 (15), 86.2 (100), 56.1 (50); Anal. Calcd for C$_{15}$H$_{13}$N$_2$Br: C, 59.82; H, 4.35; N, 9.30; Found: C, 59.39; H, 4.23; N, 9.03.

d. 1-Isopropyl-2,3-dihydro-1H-imidazo[1,2-f]phenanthridin-4-ylium (6d)

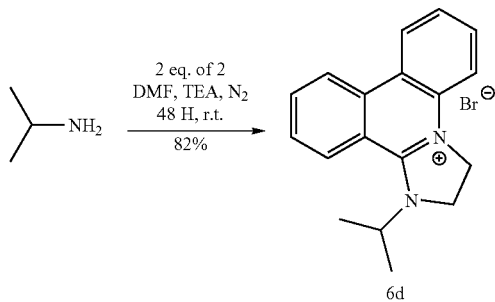

6d (267 mg; 0.78 mmol) was obtained as a yellow powder in a 82% yield; mp: 250-251° C. (dec.); $^1$H NMR (CD$_3$OD, 400 MHz): δ 8.81 (d, 1H, J=8.4 Hz), 8.62 (d, 1H, J=8.4 Hz), 8.58 (d, 1H, J=8.4 Hz), 8.12 (t, 1H, J=8.4 Hz), 7.90 (t, 1H, J=8.4 Hz), 7.82 (t, 1H, J=8.4 Hz), 7.62 (m, 2H), 5.23 (q, 1H, J=6.6 Hz), 4.76 (t, 2H, J=10.5 Hz), 4.38 (t, 2H, J=10.5 Hz), 1.62 (d, 6H, J=6.6 Hz); $^{13}$C NMR (CD$_3$OD, 100 MHz): δ 155.03 (C), 137.64 (C), 136.76 (CH), 134.96 (C), 133.02 (CH), 130.74 (CH), 129.55 (CH), 126.95 (CH), 125.81 (CH), 125.29 (CH), 122.21 (C), 117.52 (C), 116.98 (CH), 52.50 (CH), 47.51 (CH), 45.16 (CH$_2$), 21.22 (CH$_3$); IR (KBr, cm$^{-1}$): 3433(s), 2981(w), 2015(w), 1610(m), 1597(m), 1574 (s), 1550(s), 1556(w), 1303(m), 1169(w), 1126(w), 1068(w), 758(m); MS (FAB): 263.2 (M−Br) (100), 221.1 (6), 154.1 (12), 137.1 (6), 89.6 (2), 77.7 (1); Anal. Calcd for C$_{18}$H$_{19}$N$_2$Br. 0.25H$_2$O: C, 62.17; H, 5.65; N, 8.90; Found: C, 62.27; H, 6.01; N, 8.95.

e. 1-Cyclopropyl-2,3-dihydro-1H-imidazo[1,2-f]phenanthridin-4-ylium bromide (6e)

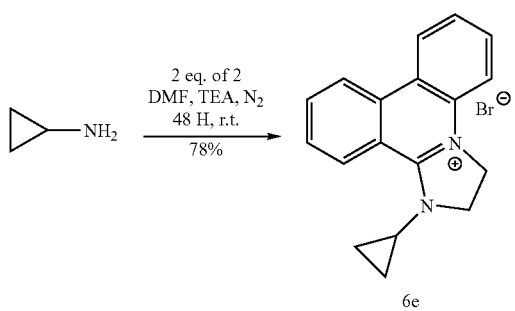

6e (250 mg; 0.74 mmol) was obtained as a white off powder in a 78% yield; mp: 129-130° C. (dec.); $^1$H NMR (D$_2$O, 400 MHz): δ 8.84 (d, 1H, J=8.4 Hz), 8.20 (d, 1H, J=8.0 Hz), 8.84 (d, 1H, J=8.0 Hz), 8.10 (d, 1H, J=8.0 Hz), 7.85 (t, 1H, J=8.0 Hz), 7.64 (m, 2H), 7.42 (t, 1H, J=8.0 Hz), 7.17 (d, 2H, J=8.0 Hz), 4.25 (t, 2H, J=11 Hz), 4.11 (t, 2H, J=11 Hz), 3.26 (qt, 1H, J=3.5 Hz), 1.21 (m, 2H), 1.03 (m, 2H); $^{13}$C NMR (D$_2$O, 100 MHz): δ 155.05 (C), 155.05 (C), 135.52 (CH), 134.87 (C), 132.43 (C), 131.55 (CH), 129.24 (CH), 128.88 (CH), 125.69 (CH), 123.55 (CH), 123.40 (CH), 119.98 (C), 115.46 (CH), 102.52 (C), 49.95 (CH$_2$), 45.77 (CH$_2$), 31.51 (CH), 10.49 (2*CH$_2$); IR (KBr, cm$^{-1}$): 3427(s), 3024(w), 2358(w), 1610(m), 1595(m), 1575(s), 1548(s), 1454(m), 1356(w), 1307(m), 1045(w), 762(m); MS (FAB): 261.1 (M−Br) (100), 219.1 (6), 154 (12), 136 (11), 120.1 (2), 89.5 (2), 77.7 (1); Anal. Calcd for C$_{18}$H$_{17}$N$_2$Br: C, 64.35; H, 5.02; N, 8.21. Found: C, 64.68; H, 5.02; N, 8.09.

f. L-alanine methoxycarbonyl derivative (6f)

6f (550 mg; 1.2 mmol) was obtained as a hygroscopic white powder in a 63% yield; 137-138° C.; $^1$H NMR (D$_2$O, 400 MHz): δ 8.13 (d, 1H, J=8.0 Hz), 8.03 (d, 1H, J=8.0 Hz), 7.87 (d, 1H, J=8.0 Hz), 7.82 (t, 1H, J=8.0 Hz), 7.62 (t, 1H, J=8.0 Hz), 7.59 (t, 1H, J=8.0 Hz), 7.44 (t, 1H, J=8.0 Hz), 7.22 (d, 1H, J=8.0 Hz), 7.05 (d, 2H, J=6.4 Hz), 6.82 (m, 3H), 5.90 (dd, 1H, J=15.6 and 4 Hz), 4.48 (m, 1H), 4.30 (m, 2H), 4.19 (m, 1H), 3.84 (s, 3H), 3.50 (dd, 1H, J=15.6 and 4 Hz), 3.24 (dd, 1H, J=15.6 and 11.2 Hz); $^{13}$C NMR (D$_2$O, 100 MHz): δ 135.96 (CH), 135.10 (C), 135.05 (C), 131.72 (CH), 131.5 (C), 129.22 (CH), 129.00 (CH), 127.80 (CH), 127.01 (CH), 126.64 (CH), 124.06 (CH), 123.51 (CH), 121.00 (CH), 120.00 (C), 115.97 (CH), 114.6 (C); MS (FAB): 383.5 (M−Br) (100), 307.3 (12), 233.2 (5), 219.2 (5), 154.1 (22), 137.1 (15); Anal. Calcd for C$_{25}$H$_{23}$BrN$_2$O$_2$: C, 64.80; H, 5.00; Br, 17.24; N, 6.05; O, 6.91.

g. Ethylene diamine derivative (6g)

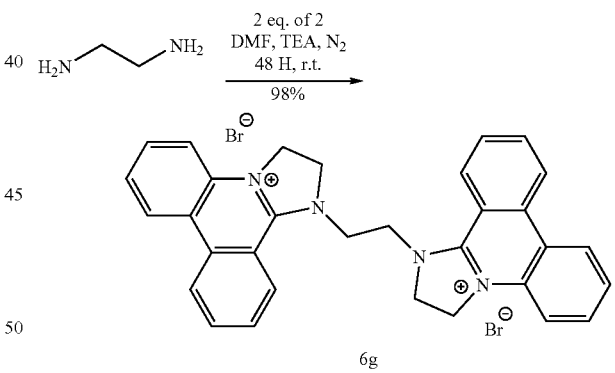

2-Bromo-ethyl-phenanthridinium bromide (2) (700 mg; 1.9 mmol) was suspended in DMF (20 ml). Ethylenediamine (31.8 μl; 0.48 mmol) and TEA (795 μl; 5.7 mmol) were added successively to the stirred solution. After stirring for 48 hours at r.t. under nitrogen, the final product and TEA hydrobromide salt were precipitated from the solution with diethyl ether (100 ml) and recovered by filtration. The precipitate washed thoroughly with diethyl ether and ethyl acetate and then triturated with 1 ml of water to remove the TEA salt, yielding 6g (295 mg; 0.47 mmol) as a yellow powder in a 98% yield; mp: >400° C.; $^1$H NMR ((CD$_3$)$_2$SO, 400 MHz): δ 8.70 (d, 2H, J=8.0 Hz), 8.66 (d, 2H, J=8.0 Hz), 8.62 (d, 2H, J=8.0 Hz), 8.01 (t, 2H, J=8.0 Hz), 7.87 (t, 2H, J=8.0 Hz), 7.78 (t, 2H, J=8.0 Hz), 7.66 (m, 4H), 4.76 (s, 4H), 4.68 (t, 4H, J=10.6 Hz), 4.50 (t, 4H, J=10.6 Hz); IR (KBr, cm$^{-1}$): 3435 (s), 1612 (m), 1597 (m), 1574 (s), 1554 (s), 1456 (w), 1311 (m), 1265 (m), 762 (m) MS (FAB): 234 ((M−2Br)/2) (5), 232 (10), 214 (5), 198 (1), 157 (35), 137 (5), 102.4 (2), 79.6 (100), 61.8 (5); Anal. Calcd for $C_{32}H_{28}N_4Br_2 \cdot H_2O$: C, 59.46; H, 4.68; N, 8.67. Found: C, 59.80; H, 4.42; N, 8.31.

h. Tris(2-aminoethyl)amine derivative (6h)

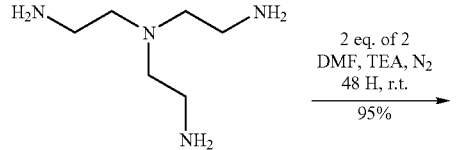

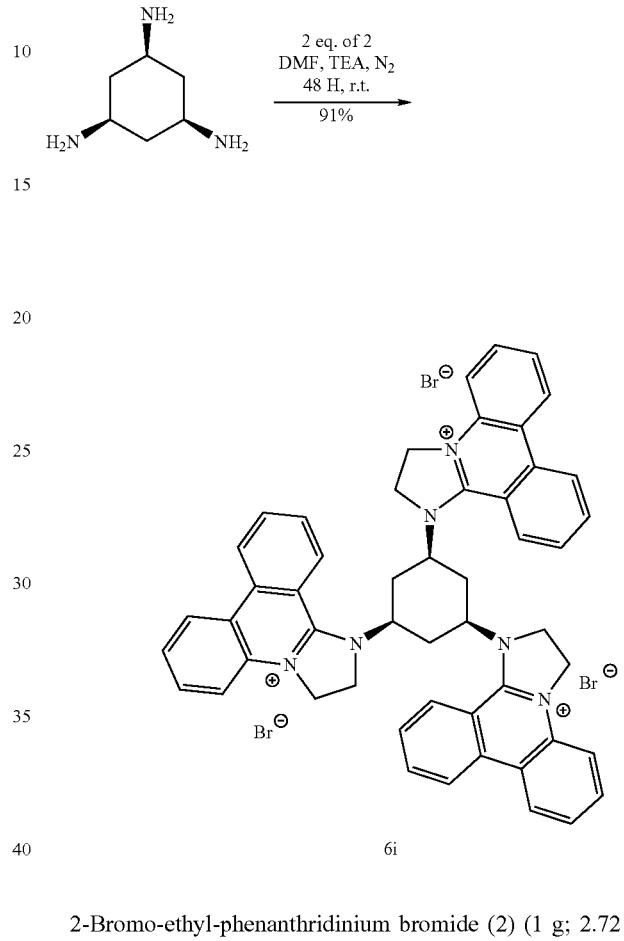

2-Bromo-ethyl-phenanthridinium bromide (2) (1 g; 2.72 mmol) was suspended in DMF (50 ml). Tris(2-aminoethyl) amine (68 μl; 0.454 mmol) and TEA (1.15 ml; 8.2 mmol) were added successively to the stirred solution. After stirring for 48 hours at r.t. under nitrogen, the final product and TEA hydrobromide salt were precipitated from the solution with diethyl ether (100 ml) and recovered by filtration. The precipitate washed thoroughly with diethyl ether and ethyl acetate and then triturated with 1 ml of water to removed the TEA salt, yielding 6h (430 mg; 0.43 mmol) as a yellow powder in a 95% yield; mp: 326-327° C.; $^1$H NMR ((CD$_3$)$_2$SO, 400 MHz): δ 8.61 (d, 3H, J=8.0 Hz), 8.51 (d, 3H, J=8.0 Hz), 8.43 (d, 3H, J=8.0 Hz), 7.94 (t, 3H, J=8.0 Hz), 7.82 (m, 6H), 7.57 (t, 3H, J=8.0 Hz), 7.51 (d, 3H, J=8.0 Hz), 4.57 (t, 6H, J=10.0 Hz), 4.44 (t, 6H, J=10.0 Hz), 4.35 (m, 6H), 3.35 (m, 6H); $^{13}$C NMR ((CD$_3$)$_2$SO, 100 MHz): δ 153.55 (C), 135.43 (C), 134.81 (CH), 132.72 (C), 131.78 (CH), 129.50 (CH), 127.69 (CH), 125.67 (CH), 124.31 (CH), 124.08 (CH), 119.79 (C), 116.09 (C), 115.25 (CH), 51.76 (CH$_2$), 51.46 (CH$_2$), 49.19 (CH$_2$), 46.25 (CH$_2$); IR (KBr, cm$^{-1}$): 3435 (s), 2925 (w), 2358 (w), 1610 (s), 1575 (s), 1456 (m), 1384 (w), 1304 (m), 1267 (m), 1106 (w), 750 (w), 717 (w), 667 (w); Anal. Calcd for $C_{51}H_{48}Br_3N_7$: C, 61.34; H, 4.84; N, 9.82; Found: C, 61.11; H, 4.90; N, 9.62.

i. cis-1,3,5-Triaminocyclohexane derivative (6i)

2-Bromo-ethyl-phenanthridinium bromide (2) (1 g; 2.72 mmol) was suspended in DMF (30 ml). Cis-1,3,5-Triaminocyclohexane (58 mg; 0.45 mmol) and TEA (1.15 ml; 8.16 mmol) were added successively to the stirred solution. After stirring for 48 hours at r.t. under nitrogen, the final product and TEA hydrobromide salt were precipitated from the solution with diethyl ether (100 ml) and recovered by filtration. The precipitate washed thoroughly with diethyl ether and ethyl acetate and then triturated with 1 ml of water to removed the TEA salt, yielding 6i (400 mg; 0.41 mmol) as a yellow powder in a 91% yield; mp: 360° C. (dec.); $^1$H NMR ((CD$_3$)$_2$SO, 400 MHz): δ 9.11 (d, 3H, J=8.4 Hz), 8.91 (d, 3H, J=8.4 Hz), 8.73 (d, 3H, J=8.0 Hz), 8.18 (t, 3H, J=5.1 Hz), 8.04 (t, 3H, J=5.1 Hz), 7.86 (t, 3H, J=5.1 Hz), 7.70 (d, 3H, J=8.0 Hz), 7.64 (t, 3H, J=5.1 Hz), 5.93 (m, 3H), 4.79 (t, 6H, J=6.9 Hz), 4.53 (t, 6H, J=6.9 Hz), 2.82 (q, 3H, J=11.6 Hz), 2.6 (d, 3H, J=11.6 Hz); $^{13}$C NMR ((CD$_3$)$_2$SO, 100 MHz): δ 156.31 (CH), 135.53 (CH), 135.25 (C), 133.11 (CH), 131.82 (CH), 130.40 (CH), 129.17 (CH), 125.80 (C), 124.68 (CH), 124.23 (C), 120.41 (CH), 116.32 (C), 115.85 (CH), 52.66 (CH$_2$), 46.25 (CH$_2$), 45.54 (CH), 32.43 (CH$_2$); IR (KBr, cm$^{-1}$): 3421 (s), 1610 (s), 1570 (s), 1533 (s), 1452 (m), 1386 (w), 1304 (s), 1263 (s), 1155 (m), 1122 (m), 783 (m), 754 (s), 717 (m), 669 (m); MS (FAB): 247.14 ((M−3*Br)/3) (5), 232.1 (11), 219.11 j. 1-(4-Methoxy-phenyl)-2,3-dihydro-1H-imidazo[1,2-f]phenanthridin-4-ylium bromide (6j)

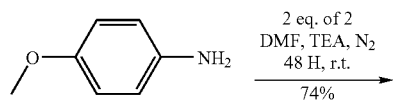

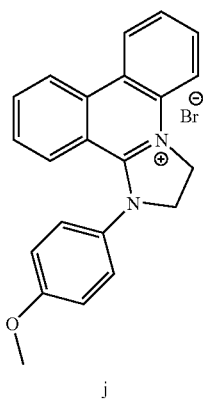

6j (285 mg; 0.7 mmol) was obtained as a pale green powder in a 74% yield; mp: 368-369° C. (dec.); $^1$H NMR ((CD$_3$)$_2$SO, 400 MHz): δ 8.90 (d, 1H, J=8.0 Hz), 8.80 (d, 1H, J=8.0 Hz), 0.05 (t, 1H, J=8.0 Hz), 7.91 (t, 1H, J=8.0 Hz), 7.82 (d, 1H, J=8.0 Hz), 7.67 (m, 3H), 7.58 (t, 1H, J=8.0 Hz), 7.35 (d, 1H, J=8.0 Hz), 7.24 (d, 2H, J=8.0 Hz), 4.92 (t, 2H, J=9.8 Hz), 4.56 (t, 2H, J=9.8 Hz), 3.88 (s, 3H); $^{13}$C NMR ((CD$_3$)$_2$SO, 100 MHz): δ 160.42 (C), 152.98 (C), 135.59 (CH), 135.36 (C), 133.03 (C), 131.90 (CH), 131.88 (CH), 129.02 (CH), 128.51 (CH), 128.50 (CH), 127.29 (CH), 125.98 (CH), 124.64 (CH), 124.43 (CH), 120.63 (C), 120.62 (C), 116.45 (CH), 116.30 (CH), 115.77 (C), 56.02 (CH$_3$), 55.01 (CH$_2$), 47.09 (CH$_2$); IR (KBr, cm$^{-1}$): 3435(s), 29232(w), 2360(w), 1610(s), 1577(s), 1554(m), 1512(m), 1456(w), 1298(w), 1251(s), 1028(m), 764(m); MS (FAB): 327.1 (M−Br) (100), 307.1 (20), 289.1 (10), 261.1 (2), 219.1 (2), 154 (80), 136 (50), 107.3 (16), 89.5 (14), 77.6 (12), 65.8 (5), 52 (5); Anal. Calcd for C$_{22}$H$_{19}$N$_2$OBr. H$_2$O: C, 62.13; H, 4.98; N, 6.59. Found: C, 62.21; H, 4.46; N, 6.60.

k. 1-Phenyl-2,3-dihydro-1H-imidazo[1,2-f]phenanthridin-4-ylium bromide (6k)

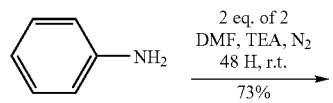

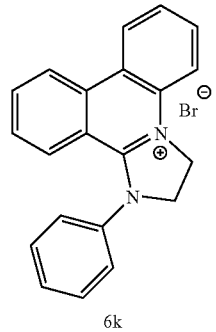

6k (260 mg; 0.695 mol) was obtained as a yellow powder in a 73% yield; mp: 355-356° C. (dec.); $^1$H NMR (CD$_3$OD, 400 MHz): δ 8.85 (d, 1H, J=8.4 Hz), 8.75 (d, 1H, J=8.4 Hz), 8.05 (t, 1H, J=8.4 Hz), 7.93 (t, 1H, J=8.4 Hz), 7.81 (d, 1H, J=8.4 Hz), 7.71 (m, 6H), 7.45 (m, 2H), 5.04 (t, 2H, J=10.4 Hz), 4.69 (t, 2H, J=10.4 Hz); $^{13}$C NMR (CD$_3$OD, 100 MHz): δ 154.87 (C), 144.05 (C), 141.02 (CH), 137.69 (CH), 137.07 (CH), 134.63 (C), 133.20 (CH), 132.60 (CH), 132.02 (CH), 129.94 (CH), 129.24 (CH), 128.47 (CH), 126.45 (CH), 125.76 (CH), 122.72 (C), 120.46 (C), 117.43 (CH), 117.00 (C), 56.19 (CH$_2$), 48.76 (CH$_2$); IR (KBr, cm$^{-1}$): 3434 (s), 3047 (w), 1612 (m), 1599 (m), 1575 (s), 1545 (s), 1485 (w), 1440 (m), 1309 (s), 1171 (w), 935(w), 758 (s); MS (FAB): 297 (M−Br) (100), 269 (2), 230 (8), 219 (4), 178 (4), 154 (6), 136 (5), 107.2 (1), 77.6 (2); Anal. Calcd for C$_{21}$H$_{17}$N$_2$Br 0.5H$_2$O: C, 65.30; H, 4.70; N, 7.25. Found: C, 65.71; H, 4.53; N, 7.11.

Alternative Synthesis of Compounds Represented by Formula A

In an alternative method for producing the compounds of the invention an oxidizing agent, such as N-bromo-succinimide, was used to avoid the consumption of an equivalent of the phenanthridinium starting material, and a biphasic solution of water/ethyl acetate was employed to facilitate the isolation of the non-oxidized 5-membered ring as well as the elimination of the base and its HBr salt. A solution of triethanolamine (557 μl; 4 mmol), Sodium hydrogen carbonate (3 g; 35.7 mmol) and primary amine (2.1 mmol) in ethyl acetate (40 ml) and water (40 ml) was prepared in a round bottom flask. 2-Bromo-ethyl-Phenanthridinium (700 mg; 1.9 mmol) was added under nitrogen to the stirred solution at 0° C. The solution was left stirring and worming-up to r.t., under nitrogen, for 2 H. The organic layer was separated, washed three times with water and placed into a round bottom flask cover with aluminium foil. N-Bromosuccinimide (373.8 mg; 2.1 mmol) was added to the stirred solution at 0° C. and the reaction mixture was left stirring and worming-up to r.t, overnight, in the dark. The final product precipitated from the solution was removed by filtration and washed with diethyl ether to yield the corresponding DIP framework.

Formula B Compounds

1. Preparation of 5-(2-Piperidin-1-yl-ethyl)-phenanthridinium bromide 14a

2-Bromo-ethyl-phenanthridinium bromide (700 mg; 1.9 mmol) was dissolved in 20 ml DMF. Piperidine (179 mg; 208 μl; 2.1 mmol) and TEA (0.576 mg; 795 μl; 5.7 mmol) were added successively to the stirred solution. After stirring for 48 H at r.t. under nitrogen, the final product and TEA hydrobromide salt were precipitated from the solution with diethyl ether (50 ml) and this was recovered by filtration. The precipitate washed thoroughly with diethyl ether and ethyl acetate and then triturated with 1 ml of water to get ride of the TEA salt to obtain 14a (500 mg; 1.35 mmol) as a pale yellow powder in a 71% yield; mp: 167-168° C.; 1H NMR (D2O, 400 MHz): δ 9.80 (s, 1H), 8.90 (d, 1H, J=7.2 Hz), 8.83 (d, 1H, J=8.4 Hz), 8.41 (d, 1H, J=8 Hz), 8.28 (m, 2H), 7.99 (m, 3H), 5.15 (t, 2H, J=7.2 Hz), 3.04 (t, 2H, J=7.2 Hz), 2.56 (m, 4H), 1.50 (m, 4H), 1.41 (m, 2H); 13C NMR (D2O, 100 MHz): δ 154.63 (CH), 147.71 (C), 138.61 (CH), 136.45 (C), 135.35 (C), 132.72 (CH), 132.47 (CH), 130.67 (CH), 126.56 (CH), 125.11 (CH), 123.83 (C), 123.04 (CH), 119.06 (CH), 56.40 (CH2), 54.87 (CH2), 54.18 (CH2), 25.11 (CH2), 23.42 (CH2); IR (KBr, cm−1): 3448 (s), 2923 (m), 2852 (w), 2794 (w), 2360 (w), 1628 (s), 1535 (w), 1506 (w), 1454 (m), 1352 (w), 1257 (w), 1161 (w), 1122 (w), 1036 (w), 769 (s); MS (FAB): 291.2 (M−Br) (100); 273.1 (4), 206.1 (7), 193 (7), 154 (92), 137 (60), 136 (60), 112.3 (45), 98.4 (16), 89.5 (11), 77.6 (5), 56.9 (2), 52 (2); Anal. Calcd for $C_{20}H_{23}N_2Br$: C, 64.69; H, 6.24; N, 7.54. Found: C, 64.17; H, 6.10; N, 7.58.

2. Preparation of Piperazine derivative 14b

2-Bromo-ethyl-phenanthridinium bromide (700 mg; 1.9 mmol) was dissolved in 20 ml DMF. Piperazine (81.8 mg; 0.95 mmol) and TEA (0.576 mg; 795 µl; 5.7 mmol) were added successively to the stirred solution. After stirring for 48 H at r.t. under nitrogen, the final product and TEA hydrobromide salt were precipitated from the solution with diethyl ether (50 ml) and this was recovered by filtration. The precipitate washed thoroughly with diethyl ether and ethyl acetate and then triturated with 1 ml of water to get ride of the TEA salt to obtain 14b (450 mg; 0.7 mmol) as a yellow powder in a 73% yield; mp: 260-261° C.; 1H NMR (D20, 400 MHz): δ 9.80 (s, 2H), δ 8.95 (d, 2H, J=8.0 Hz), δ 8.88 (d, 2H, J=8.0 Hz), δ 8.42 (d, 2H, J=8.0 Hz), δ 8.33 (d, 2H, J=8.0 Hz), δ 8.29 (t, 2H, J=8.0 Hz), δ 8.01 (m, 6H), δ 5.14 (t, 4H, J=6.8 Hz), δ 3.05 (t, 4H, J=6.8 Hz), δ 2.57 (s, 8H); 13C NMR (D2O, 100 MHz): δ 155.94 (CH), δ 138.46 (CH), δ 134.63 (C), δ 133.28 (CH), δ 133.07 (C), δ 132.41 (CH), δ 130.89 (CH), δ 130.54 (CH), δ 126.03 (C), δ 125.48 (CH), δ 123.66 (CH), δ 120.19 (CH), δ 55.43 (CH2), δ 55.08 (CH2), δ 52.95 (CH2); IR (KBr, cm−1): 3430.74 (s), 2923 (w), 2360 (w), 1626 (s), 1456 (m), 1261 (w), 1026 (w), 758 (w); MS (FAB): 498.4 (M−2Br) (60), 318.2 (30), 292.1 (50), 249.1 (80), 206.1 (70), 154.0 (100), 136.0 (80), 112.3 (35), 56.9 (30); Anal. Calcd for $C_{34}H_{34}N_4Br_2$: C, 62.01; H, 5.20; N, 8.51; Found: C, 62.30; H, 5.45; N, 8.51.

3. Preparation of the Triazacyclododecane derivative 14c

2-Bromo-ethyl-phenanthridinium bromide (700 mg; 1.9 mmol) was dissolved in 20 ml DMF. 1,5,9triaza-Cyclododecane (108 mg; 0.63 mmol) and TEA (0.576 mg; 795 µl; 5.7 mmol) were added successively to the stirred solution. After stirring for 48 H at r.t. under nitrogen, the final product and TEA hydrobromide salt were precipitated from the solution with diethyl ether (50 ml) and this was recovered by filtration. The precipitate washed thoroughly with diethyl ether and ethyl acetate and then triturated with 1 ml of water to get ride of the TEA salt to obtain 14c (605 mg; 0.59 mmol) as a yellow powder in a 93% yield; $^1$H NMR (CD$_3$OD, 400 MHz): δ 9.93 (s, 3H), 8.99 (t, 6H, J=8.8 Hz), 8.45 (d, 3H, J=8.0 Hz), 8.42 (d, 3H, J=6.8 Hz), 8.30 (t, 3H, J=7.6 Hz), 8.00 (m, 6H), 7.85 (t, 3H, J=7.6 Hz), 5.02 (m, 6H), 2.57 (m, 6H), 1.41 (m, 12H), 0.05 (m, 6H); $^{13}$C NMR (CD$_3$OD, 100 MHz): δ 156.53 (CH), 140.11 (CH), 136.93 (C), 135.00 (C), 134.23 (CH), 133.95 (CH), 132.28 (CH), 132.19 (CH), 128.13 (C), 126.71 (CH), 125.14 (C), 124.85 (CH), 121.43 (CH), 57.57 (CH$_2$), 53.34 (CH$_2$), 49.39 (CH$_2$), 23.25 (CH$_2$).

4. Preparation of 5-[2-(4-Methoxy-benzylsulfanyl)-ethyl]-phenanthridinium bromide 15

2-Bromo-ethyl-phenanthridinium bromide (700 mg; 1.9 mmol) was dissolved in 20 ml DMF. (4-Methoxy-phenyl)-methanethiol (324 mg; 208 µl; 2.1 mmol) and TEA (0.576 mg; 795 µl; 5.7 mmol) were added successively to the stirred solution. After stirring for 48 H at r.t. under nitrogen, the final product and TEA hydrobromide salt were precipitated from the solution with diethyl ether (50 ml) and, this was recovered by filtration. The precipitate was washed thoroughly with diethyl ether and ethyl acetate and then triturated with 1 ml of water to get ride of the TEA salt to obtain 9 (500 mg; 1.35 mmol) as a pale yellow powder in a 76% yield; mp: 182-183° C.; 1H NMR (CD3OD, 400 MHz): δ 9.91 (s, 1H), δ 9.08 (t, 2H, J=8.0 Hz), δ 8.85 (d, 1H, J=8.0 Hz), δ 8.47 (t, 1H, J=8.0 Hz), δ 8.37 (m, 1H), δ 8.15 (t, 1H, J=8.0 Hz), δ 8.11 (m, 2H), δ 6.80 (d, 2H, J=8.8 Hz), δ 6.33 (d, 2H, J=8.8 Hz), δ 5.17 (t, 2H, J=6.0 Hz), δ 4.90 (t, 2H, J=6.0 Hz), δ 3.69 (s, 3H), δ 3.56 (s, 2H); 13C NMR (CD3OD, 100 MHz): δ 161.8 (C), δ 156.84 (C), δ 140.00 (CH), δ 137.21 (C), δ 134.41 (CH), δ 133.77 (CH), δ 132.07 (CH), δ 131.96 (CH), δ 131.31 (C), δ 130.96 (CH), δ 128.00 (C), δ 126.72 (CH), δ 125.21 (CH), δ 124.74 (CH), δ 120.76 (CH), δ 114.96 (CH), δ 58.90 (CH2), δ 55.92 (CH3), δ 36.97 (CH2), δ 31.70 (CH2); IR (KBr, cm−1): 3435 (s), 1626 (s), 1533 (w), 1510 (s), 1450 (m), 1304 (w), 1248 (s), 1174 (w), 1030 (s), 829 (s), 764 (s); MS (FAB): 360.0 (M−Br) (70), 309.0 (20), 290.0 (15), 238.0 (5), 206.0 (10), 179 (7), 155.0 (100), 136.0 (50), 121.1 (50), 108.2 (20), 89.5 (12); Anal. Calcd for $C_{23}H_{22}NOSBr$: C, 62.72; H, 5.03; N, 3.18; Found: C, 62.72; H, 5.01; N, 3.78.

5. Preparation of 5-(2-Bromo-ethyl)-6-piperidin-1-yl-5,6-dihydro-phenanthridine 16

In an NMR tube, 2-Bromo-ethyl-phenanthridinium bromide (2) (12.8 mg; 0.035 mmol) was dissolved in D$_2$O (0.6 ml). A 56 mM solution of piperidine in CDCl$_3$ was prepared by dissolving piperidine (5.5 µl; 56 µmol) in 995 µl CDCl$_3$. 0.6 ml of this solution (0.034 mmol) was added to the D$_2$O layer and the NMR tube was energetically shaken for 1 minute to allowed the phase transfer process to occur. Piperidine is used in default to avoid a second reaction on the less electrophilic centre of (2). Piperidine is also used as a base so only half of it should undergo the alpha addition step. A $^1$H NMR spectrum of the bottom CDCl$_3$ layer was taken, characterising (16). Note that the compound is highly unstable in solution as it undergoes intermolecular and intramolecular reactions (carbon-bromide substitution). The solution becomes yellow in minutes and the $^1$H NMR spectrum becomes quickly non-interpretable. Neither mass spectroscopy nor $^{13}$C NMR spectrum was therefore possible to obtained. $^1$H NMR (CDCl$_3$, 400 MHz): δ 7.98 (d, 1H, J=8.8 Hz), 7.93 (d, 1H, J=8.0 Hz), 7.44 (m, 2H), 7.37 (t, 1H, J=6.2 Hz), 7.28 (d, 1H, J=7.2 Hz), 6.94 (t, 1H, J=7.2 Hz), 6.82 (d, 1H, J=8.0 Hz), 5.76 (s, 1H), 4.2 (m, 2H), 3.75 (m, 1H), 3.60 (m, 1H), 1.69 (t, 4H, J=5.6), 1.45 (m, 6H).

6. Preparation of 5-(2-Bromo-ethyl)-6-(4-methoxy-benzylsulfanyl)-5, 6-dihydro-phenanthridine 17

In an NMR tube, 2-Bromo-ethyl-phenanthridinium (2) (12.6 mg; 0.034 mmol) was dissolved in D$_2$O (0.6 ml) and CDCl$_3$ (0.6 ml) was added. 4-methoxybenzyl mercaptan (4.7 µl; 0.034 mmol) was added. No reaction takes place before adding TEA as the thio-derivative is not basic enough to start the reaction. TEA (4.7 µl; 0.034 mmol) was added and the NMR tube was energetically shaken for 1 minute to allowed the phase transfer process to occur. 4-methoxybenzyl mercaptan is used in default to avoid a second reaction on the less electrophilic centre of (2). A $^1$H and $^{13}$C NMR spectrum of the bottom CDCl$_3$ layer as well as a mass spectrum were taken, characterising 17; $^1$H NMR (CDCl$_3$, 400 MHz): δ 7.83 (t, 2H, J=7.2 Hz), 7.40 (t, 1H, J=7.2 Hz) (7.30 (m, 2H), 7.21 (d, 1H, J=7.6 Hz), 7.07 (d, 2H, J=8.8 Hz), 6.98 (t, 1H, J=7.4 Hz), 6.79 (d, 2H, J=8.8 Hz), 6.75 (d, 1H, J=7.6 Hz), 5.74 (s, 1H), 4.00 (m, 1H), 3.82 (m, 1H), 3.74 (s, 3H), 3.65 (m, 2H), 3.50 (s, 2H); $^{13}$C NMR (CDCl$_3$, 100 MHz): δ 159.80 (C), 158.32 (C), 133.12 (CH), 134.33 (CH), 132.14 (CH), 130.28 (CH), 129.75 (CH), 129.12 (C), 124.71 (CH), 122.45 (C), 122.26 (CH), 120.00 (C), 119.06 (CH), 114.06 (C), 113.91 (CH), 79.10 (CH), 56.32 (CH$_2$) 55.25 (CH$_3$), 35.38 (CH$_2$), 33.62 (CH$_2$); MS (EI+): 361.4 (M−Br) (25), 240.2 (18), 219.2 (35), 194.2 (100), 180.2 (47), 166 (25), 121.2 (58), 86.2 (18).

7. Preparation of Hydrobromide salt of 5-(2-Isopropylamino-ethyl)-phenanthridinium bromide 7d 2-Bromo-ethyl-phenanthridinium (2) (700 mg; 1.9 mmol) was suspended in 20 ml of water and 20 ml of chloroform. To the stirred solution, was added isopropylamine (162.4 µl; 1.9 mmol) followed by TEA (794 µl; 5.7 mmol). The solution was left stirring at r.t. under nitrogen for 1 H. The aqueous layer was removed and the organic solution was washed twice with 20 ml water to have the non-oxidized 5 membered ring intermediate (4d) in solution (1.9 mmol; 20 ml at 95 ml). 20 ml of HBr 48% was added and the solution was stirred overnight at room temperature. 30 ml of water was added to dissolve the yellow precipitate newly formed and the aqueous layer was separated and washed twice with ethyl acetate. The aqueous solution was then concentrated under vacuum to 2 ml and precipitated by adding acetone. The precipitate was recovered by filtration and washed with ethyl acetate to yield 7d (780 mg; 1.8 mmol) as a white off powder in a 96% yield; mp: 285-286° C.; $^1$H NMR (D$_2$O, 400 MHz): δ 9.96 (s, 1H), 9.00 (2, 1H, J=8.0 Hz), 8.91 (d, 1H, J=8.0 Hz), 8.48 (d, 1H, J=8.0 Hz), 8.35 (m, 2H), 8.11 (t, 1H, J=8.0 Hz), 8.07 (d, 1H, J=8.0 Hz), 8.02 (t, 1H, J=8.0 Hz), 5.44 (t, 2H, J=7.0 Hz), 3.80 (t, 2H, J=7.0 Hz), 3.45 (sept, 1H, J=6.5 Hz), 1.25 (d, 6H, J=6.5 Hz); $^{13}$C NMR (D$_2$O, 100 MHz): δ 164.50 (C), 156.17 (CH), 139.47 (CH), 136.17 (C), 133.23 (CH), 132.87 (CH), 131.08 (CH), 130.93 (CH), 127.10 (C), 125.61 (CH), 124.05 (C), 123.34 (CH), 118.76 (CH), 54.17 (CH), 52-44 (CH$_2$), 43.04 (CH$_3$), 18.42 (CH$_2$); MS (CI+): 267.2 (M−2Br+H$^-$) (100), 265.2 (60), 195.1 (15), 180.1 (25); Anal. Calcd for C$_{18}$H$_{22}$Br$_2$N$_2$: C, 50.13; H, 5.20; N, 6.57; Found: C, 50.20; H, 5.03; N, 6.44.

8. Alternative Method B

A 7.5% NaHCO$_3$ solution (40 ml) was prepared (NaHCO$_3$ (3 g; 35.7 mmol) in 40 ml water) and ethyl acetate (40 ml) was added followed by TEA (557 µl; 4 mmol). The biphasic solution was cooled down to 0° C. and the primary amine (2.1 mmol) was added followed by AP2-7 (700 mg; 1.9 mmol). The reaction mixture was stirred under nitrogen at r.t. for 3 hours. The organic layer was separated, washed three times with water and placed into a round bottom flask cover with aluminium foil. N-Bromosuccinimide (373.8 mg; 2.1 mmol) was added to the stirred solution at 0° C. and the reaction mixture was then stirred at r.t. for 3 hours in the dark. The final product precipitated from the solution was recovered by filtration and washed with diethyl ether to yield the corresponding DIP framework.

The references mentioned herein are all expressly incorporated by reference in their entirety.

The invention claimed is:
1. A compound represented by the formula:

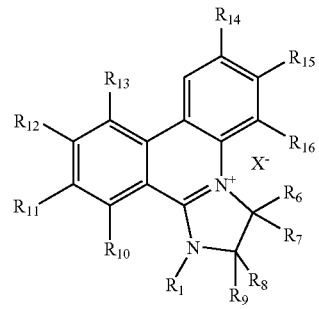

wherein:
R$_1$ is selected from hydrogen, unsubstituted or substituted C$_{1-7}$alkyl, unsubstituted or substituted C$_{1-7}$cycloalkyl, unsubstituted or substituted C$_{1-7}$cycloalkyl-C$_{1-7}$alky, unsubstituted or substituted C$_{5-20}$aryl, unsubstituted or substituted C$_{5-20}$aryl-C$_{1-7}$alkyl, unsubstituted or substituted C$_{3-20}$heterocyclyl, or a linking group to form a multimeric compound in which a plurality of compounds represented by said formula are covalently bonded together;
R$_6$ and R$_7$ are independently selected from hydrogen or independently or together can be a substituent;
R$_8$ and R$_9$ are independently selected from hydrogen or independently or together can be a substituent; and
one of the substituents R$_6$ and R$_7$ which is present on the carbon atom at the alpha position to the aromatic ring may form a double bond with one of the substituents R$_8$ and R$_9$ which is present on the carbon atom at the beta position to the aromatic ring; and
X$^{31}$ is an anionic moiety;
and wherein:
said R$_6$, R$_7$, R$_8$ and R$_9$ substituent or substituents are independently selected from halo, hydroxy, oxo, ether, formyl, C$_{1-7}$lkylacyl, C$_{5-20}$arylacyl, acylhalide, carboxy, ester, acyloxy, amido, acylamido, thioamido, tetrazolyl, amino, nitro, nitroso, azido, cyano, isocyano, cyanato, isocyanato, thiocyano, isothiocyano, sulfhydryl, thioether, sulfonic acid, sulfonate, sulfone, sulfonyloxy, sulfinyloxy, sulfamino, sulfonamino, sulfinamino, sulfamyl, sulfonamido, C$_{1-7}$alkyl, C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl, C$_{3-20}$heterocyclyl, or C$_{5-20}$aryl; and
R$_{10}$, R$_{11}$, R$_{12}$, R$_{13}$, R$_{14}$, R15 and R16 are independently selected from hydrogen, —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, -Ph, ether, ester, amido, amino, C$_{1-7}$alkyl, C$_{1-7}$haloalkyl, C$_{1-7}$hydroxyalkyl, C$_{1-7}$carboxyalkyl, C$_{1-7}$aminoalkyl, or C$_{5-20}$aryl-C$_{1-7}$alkyl.

2. The compound according to claim 1, wherein $R_1$ is a substituted $C_{1-7}$alkyl group selected from $C_{1-7}$haloalkyl, $C_{1-7}$hydroxyalkyl, $C_{1-7}$carboxyalkyl, or $C_{1-7}$aminoalkyl.

3. The compound according to claim 1, wherein $R_1$ is selected from $C_{5-20}$aryl, $C_{5-20}$carboaryl, $C_{5-20}$heteroaryl, $C_{1-7}$alkyl-$C_{5-20}$aryl or $C_{5-20}$haloaryl, optionally substituted with one or more substituents.

4. The compounds according to claim 1 which is:
  1-(4-Methoxy-benzyl)-2,3-dihydro-1H-imidazo[1,2-f]phenanthridinium bromide;
  1-(2-Hydroxy-ethyl)-2,3-dihydro-1H-imidazo[1,2-f]phenanthridin-4-ylium bromide;
  2,3-Dihydro-1H-imidazo[1,2-f]phenanthridin-4-ylium bromide;
  1-Isopropyl-2,3-dihydro-1H-imidazo[1,2-f]phenanthridin-4-ylium bromide;
  1-Cyclopropyl-2,3-dihydro-1H-imidazo[1,2-f]phenanthridin-4-ylium bromide;
  1-(4-Methoxy-phenyl)-2,3-dihydro-1H-imidazo[1,2-f]phenanthridin-4-ylium bromide;
  1-Phenyl-2,3-dihydro-1H-imidazo[1,2-f]phenanthridin-4-ylium bromide;
  1-paramethoxyaniline-2,3-dihydro-1H-imidazo[1,2-f]phenanthridin-4-ylium bromide;
  1-Methoxycarbonylmethyl-2,3-dihydro-1H-imidazo[1,2-f]phenanthridin-4-ylium bromide;
  1-(1-Methoxycarbonyl-2-phenyl-ethyl)-2,3-dihydro-1H-imidazo[1,2-f]phenanthridin-4-ylium bromide;
  1-Benzyl-2,3-dihydro-1H-imidazo[1,2-f]phenanthridin-4-ylium bromide;
  1-(2-Mercapto-ethyl)-2,3-dihydro-1H-imidazo[1,2-f]phenanthridin-4-ylium bromide;
  Propyl-2,3-dihydro-1H-imidazo[1,2-f]phenanthridin-4-ylium bromide;
  1-(2-Hydroxy-1-methyl-ethyl)-2,3-dihydro-1H-imidazo[1,2-f]phenanthridin-4-ylium bromide;
  1[1-(4-Methoxy-phenyl)-ethyl]-2,3-dihydro-1H-imidazo[1,2-f]phenanthridin-4-ylium bromide;
  7-Bromo-1-(4-methoxy-benzyl)-2,3-dihydro-1H-imidazo[1,2-f]phenanthridin-4-ylium bromide;
  1-(4-Ethyl-phenyl)-2,3-dihydro-1H-imidazo[1,2-f]phenanthridin-4-ylium bromide;
  1-Hexyl-2,3-dihydro-1H-imidazo[1,2-f]phenanthridin-4-ylium bromide;
  1-Dodecyl-2,3-dihydro-1H-imidazo[1,2-f]phenanthridin-4-ylium bromide;
  1-Octadecyl-2,3-dihydro-1H-imidazo[1,2-f]phenanthridin-4-ylium bromide; or
  1(3,3-Diphenyl-propyl)-2,3-dihydro-1H-imidazo[1,2-f]phenanthridin-4-ylium bromide;

5. The compound according to claim 1, wherein $X^{31}$ the anionic moiety is selected from halogen, tosylate or mesylate.

6. The compound according to claim 1, wherein the compounds of said formula forming the multimeric compound are covalently bonded together via their respective $R_1$ substituents or via a spacer group.

7. A multimeric compound formed by covalently linking two or more of the same or different compounds of said formula according to claim 1.

8. The multimeric compound according to claim 7, wherein compounds of said formula are linked via the $R_1$ substituent.

9. The multimeric compound according to claim 7, wherein compounds of said formula are covalently bonded via a linker group or linker groups.

10. The multimeric compound according to claim 9, wherein the linker groups is a $C_{1-7}$ alk-di-yl group bonded to another group of said formula in place of $R_1$ thereof; a piperazin-di-yl group bonded to another group of said formula in place of $R_1$ thereof; a (N,N—$C_{1-6}$ dialkylene) $C_{1-7}$ alkylene amine bonded to two other groups of said formula in place of $R_1$ thereof.

11. The multimeric compound according to claim 7, wherein the multimeric compound is a dimer, trimer or tetramer.

12. The multimeric compound according to claim 7, wherein the compounds of said formula are covalently bonded to a spacer group.

13. The multimeric compound according to claim 10 in which 2 or more compounds represented by said formula are covalently linked via one or more spacer groups.

14. The multimeric compound according to claim 10, wherein the spacer group is a polyamine compound comprising an alkyl chain having a plurality of amine groups for reacting with the compounds of said formula.

15. A composition comprising one or more compounds according to claim 1 and a pharmaceutically acceptable carrier.

16. A method for the treatment of ovarian cancer, said method comprising administering to a patient in need of said treatment a therapeutically effective amount of a compound as claimed in claim 1.

17. A method for making a compound represented by the formula of claim 1 which comprises:
  reacting a heterocyclic aromatic compound of the formula:

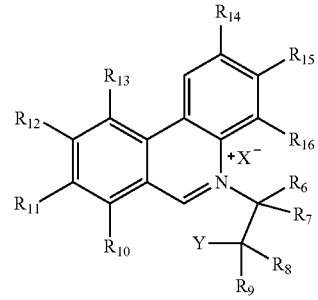

wherein Y is a leaving group and the remaining substituents are as defined in claim 1;
  with a primary amine;
  the primary amine reacting with said heterocyclic aromatic compound by addition, cyclisation and oxidation to produce a compound represented by said formula of claim 1.

18. The method according to claim 17, wherein the method uses a primary amine which (1) has no substituents in the alpha position, or (2) has a primary carbon in the alpha position, or (3) has a secondary carbon in the alpha position), or (4) has a tertiary carbon in the alpha position, or (5) is or derives from an amino acid.

19. The method according to claim 17, wherein the primary amine is an aromatic amines.

20. The method according to 17, wherein the reaction is a one pot reaction.

21. The method according to claim 17, further comprising the step of forming a multimeric compound.

22. The multimeric compound according to claim 7, wherein the compound is a dimer selected from the group of an ethylene diamine derivative with two groups of said formula; dihydro-imidazo-phenanthidinium (DIP) dimer derived from the spacer N1-(2-Amino-ethyl)-ethane-1,2-diamine; DIP dimer derived from the spacer 2-Amino-1[4-(2-amino-acetyl)-piperazin-1-yl]ethanone; DIP dimer derived from the spacer 2-[4-(2-Amino-ethyl)-piperazin-1-yl]-ethylamine; and phenanthridinium dimer derived from the spacer 2-[4-(2-Amino-ethyl)-piperazin-1-yl]-ethylamine.

23. The multimeric compound according to claim 7, wherein the compound is a trimer selected from the group of tris (2-aminoethylamine) derivatives with three groups of said formula; cis-triaminocyclohexane derivatives with three groups of said formula;

2-Amino-1-[5,9-bis-(2-amino-acetyl)-1,5,9triaza-cyclododec-1-yl]-ethanone derivative with three groups of said formula; 2-[5,9-Bis-(2-amino-ethyl)-1,5,9triaza-cyclododec-1-yl]-ethylamine derivative with three groups of said formula; dihydro-imidazo-phenanthidinium (DIP) trimer derived from the spacer 2-Amino-1-[5,9-bis-(2-amino-acetyl)-1,5,9triaza-cyclododec-1-yl]-ethanone; DIP trimer derived from the spacer Cyclohexane-1,3,5-triamine; and phenanthridinium trimer derived from the spacer 2-[5,9-Bis-(2-amino-ethyl)-1,5,9triaza-cyclododec-1-yl]-ethylamine.

24. The multimeric compound according to claim 7, wherein the compound is a tetrakis-(6-amino-hexyl)-ammonium bromide derivative with four groups of said formula.

25. The method according to claim 19, wherein said aromatic amine is naphthalene-1-ylamine or anthracin-9-ylamine.

* * * * *